US011596431B2

(12) United States Patent
Gowski et al.

(10) Patent No.: US 11,596,431 B2
(45) Date of Patent: Mar. 7, 2023

(54) APPARATUS WITH DEPLOYABLE PROBE AND BLADE AND METHODS OF USE

(71) Applicants: William F. Gowski, Salt Lake City, UT (US); Roy M. Taylor, Salt Lake City, UT (US)

(72) Inventors: William F. Gowski, Salt Lake City, UT (US); Roy M. Taylor, Salt Lake City, UT (US)

( * ) Notice: Subject to any disclaimer, the term of this patent is extended or adjusted under 35 U.S.C. 154(b) by 321 days.

(21) Appl. No.: 16/851,784

(22) Filed: Apr. 17, 2020

(65) Prior Publication Data

US 2020/0305920 A1 Oct. 1, 2020

Related U.S. Application Data

(63) Continuation-in-part of application No. PCT/US2018/012354, filed on Jan. 4, 2018, and a continuation-in-part of application No. 15/399,425, filed on Jan. 5, 2017, now Pat. No. 10,677,837, said application No. PCT/US2018/012354 is a continuation of application No. 15/399,425, filed on Jan. 5, 2017, now Pat. No. 10,667,837.

(60) Provisional application No. 62/506,924, filed on May 16, 2017.

(51) Int. Cl.
*A61B 17/32* (2006.01)
*A61B 1/00* (2006.01)

(52) U.S. Cl.
CPC ............ *A61B 17/320036* (2013.01); *A61B 17/320016* (2013.01); *A61B 1/00087* (2013.01); *A61B 1/00098* (2013.01); *A61B 2017/32004* (2013.01)

(58) Field of Classification Search
CPC ....... A61B 17/29; A61B 17/295; A61B 17/32; A61B 17/3211; A61B 17/320016; A61B 17/320036; A61B 2017/32004; A61B 2017/32044; A61B 2017/32113; A61B 17/1608
See application file for complete search history.

(56) References Cited

U.S. PATENT DOCUMENTS

| 4,962,770 | A |   | 10/1990 | Agee et al. |
| 4,963,147 | A | * | 10/1990 | Agee ............... A61B 17/320036 606/170 |
| 5,089,000 | A |   | 2/1992  | Agee et al. |
| 5,306,284 | A | * | 4/1994  | Agee ............... A61B 17/320036 606/170 |
| 5,586,990 | A |   | 12/1996 | Hahnen et al. |

(Continued)

OTHER PUBLICATIONS

European Search Report and Search Opinion Received for EP Application No. 18736404.7, dated Jul. 20, 2020, 7 pages.

(Continued)

*Primary Examiner* — Ashley L Fishback
*Assistant Examiner* — Christian D Knauss
(74) *Attorney, Agent, or Firm* — Workman Nydegger

(57) ABSTRACT

A device includes a handle, an apparatus for probing and cutting, and an adaptor. The handle includes one or more triggers. The apparatus for probing and cutting is connectable to the handle and includes an elongated member, a probe, and a blade. The probe and the blade are selectively deployable from the elongate member via activation of the one or more triggers on the handle. The adaptor is configured to selectively connect the apparatus to the handle in a predetermined orientation.

19 Claims, 16 Drawing Sheets

(56) References Cited

U.S. PATENT DOCUMENTS

| | | | |
|---|---|---|---|
| 5,709,680 | A | 1/1998 | Yates et al. |
| 8,827,135 | B2 | 9/2014 | Amid et al. |
| 8,951,273 | B1 * | 2/2015 | Fard ............... A61B 17/320036 600/104 |
| 10,667,837 | B2 | 6/2020 | Gowski |
| 2002/0099375 | A1 | 7/2002 | Hess et al. |
| 2005/0192633 | A1 | 9/2005 | Montpetit |
| 2008/0195128 | A1 * | 8/2008 | Orbay ................ A61B 17/3421 600/183 |
| 2008/0228213 | A1 | 9/2008 | Blakeney et al. |
| 2008/0312652 | A1 | 12/2008 | Bell et al. |
| 2009/0043305 | A1 | 2/2009 | Brodbeck et al. |
| 2010/0318103 | A1 | 12/2010 | Cheng et al. |
| 2013/0197516 | A1 | 8/2013 | Kappel et al. |
| 2014/0277042 | A1 * | 9/2014 | Racenet ......... A61B 17/320016 606/170 |
| 2015/0012024 | A1 | 1/2015 | Stien et al. |
| 2016/0262750 | A1 | 9/2016 | Hausen et al. |
| 2017/0095251 | A1 | 4/2017 | Thompson et al. |
| 2017/0143408 | A1 | 5/2017 | Worrell |

OTHER PUBLICATIONS

International Search Report and Written Opinion dated Mar. 22, 2018 from International Patent Application No. PCT/US2018/012354 filed Jan. 4, 2018.
Notice of Allowance and Fees Due (PTOL-85) dated Jan. 27, 2020 for U.S. Appl. No. 15/399,425.
Office Action dated Apr. 17, 2019 from U.S. Appl. No. 15/399,425, filed Jan. 5, 2017.
Office Action dated Aug. 6, 2019 from U.S. Appl. No. 15/399,425, filed Jan. 5, 2017.
Office Action dated Feb. 5, 2019 from U.S. Appl. No. 15/399,425, filed Jan. 5, 2017.
Office Action dated Jun. 20, 2018 from U.S. Appl. No. 15/399,425, filed Jan. 5, 2017.

* cited by examiner

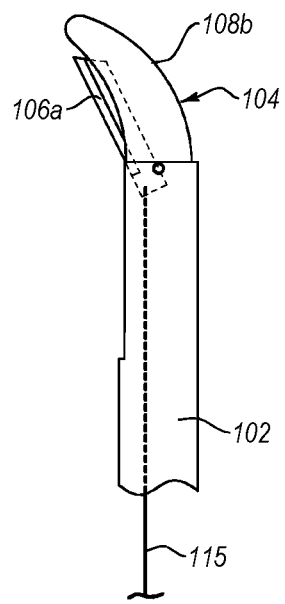 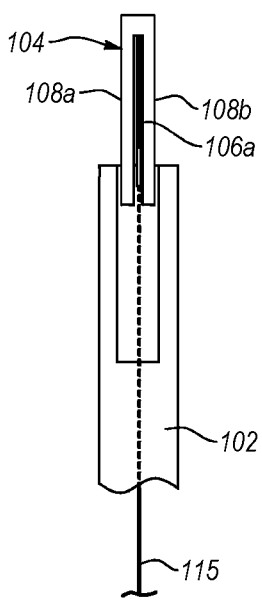 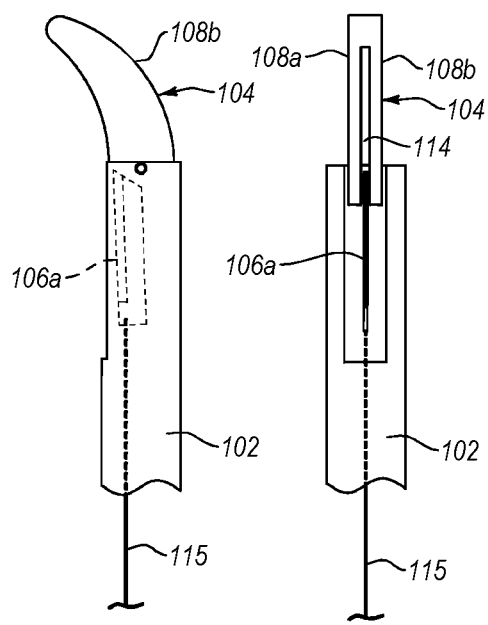 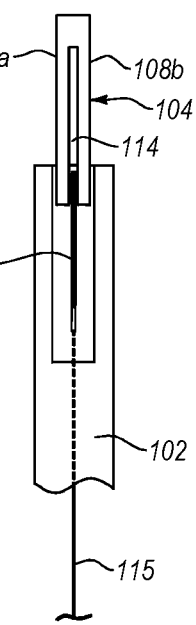
FIG. 3A  FIG. 3B  FIG. 3C  FIG. 3D
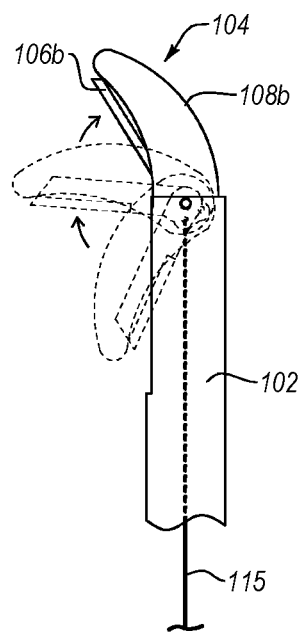 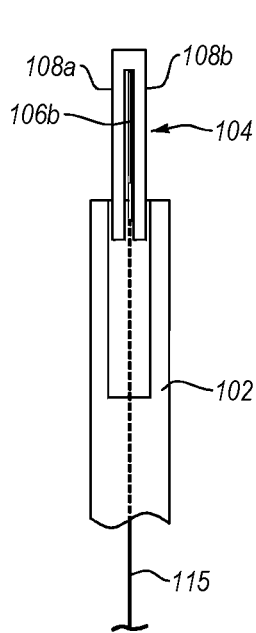 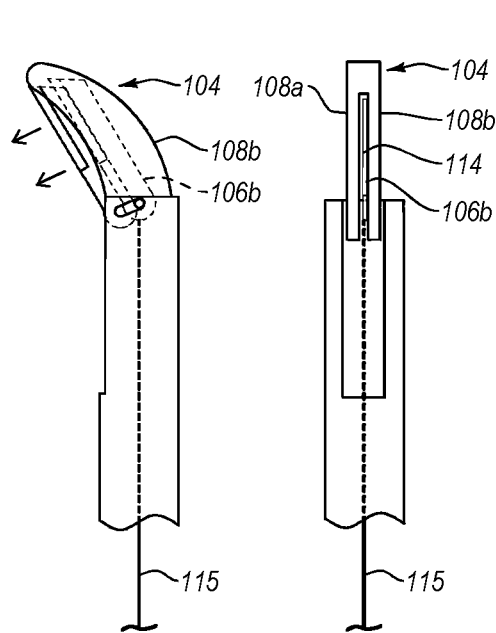 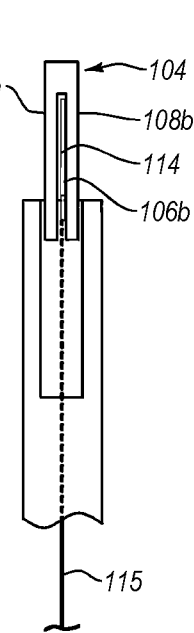
FIG. 4A  FIG. 4B  FIG. 4C  FIG. 4D

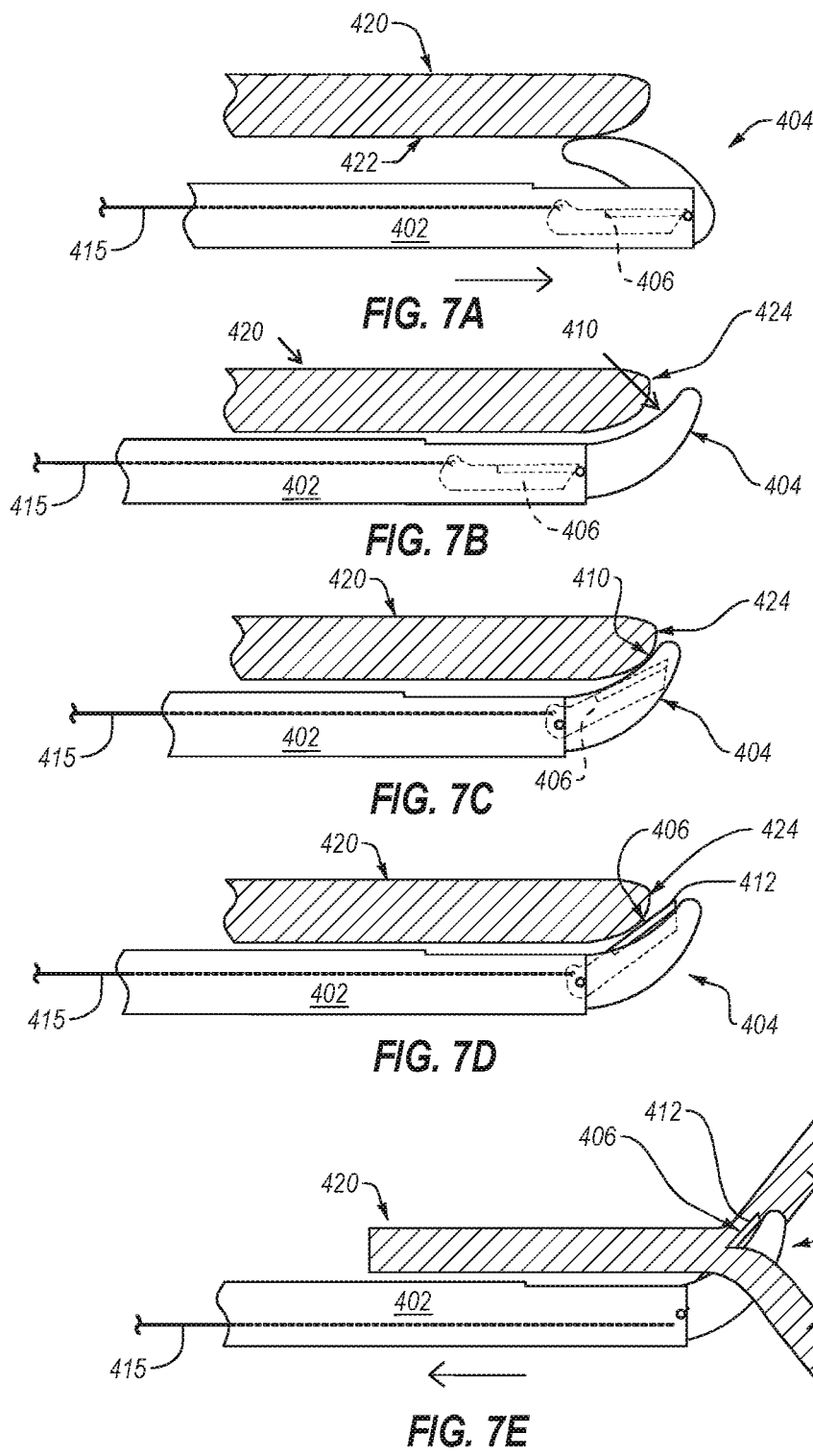

APPARATUS WITH DEPLOYABLE PROBE AND BLADE AND METHODS OF USE

CROSS-REFERENCE TO RELATED APPLICATIONS

This application is a continuation in part of U.S. patent application Ser. No. 15/399,425, filed Jan. 5, 2017, and APPARATUS WITH DEPLOYABLE PROBE AND BLADE AND METHODS OF USE. This application is also a continuation in part of International Patent Application No. PCT/US2018/012354, filed Jan. 4, 2018, and entitled APPARATUS WITH DEPLOYABLE PROBE AND BLADE AND METHODS OF USE, which claims priority to U.S. Provisional Patent Application No. 62/506,924, filed May 16, 2017, and entitled APPARATUS WITH DEPLOYABLE PROBE AND BLADE AND METHODS OF USE, and to U.S. patent application Ser. No. 15/399,425, filed Jan. 5, 2017, and entitled APPARATUS WITH DEPLOYABLE PROBE AND BLADE AND METHODS OF USE. The foregoing applications are incorporated herein by reference in their entirety.

BACKGROUND

Technical Field

This disclosure generally relates to apparatuses for probing and cutting and associated methods of use. More specifically, the present disclosure relates to apparatuses comprising a deployable probe for locating a target to be cut and a deployable blade for cutting said target and associated methods of using said apparatuses.

Related Technology

Tools for cutting include, for example, knives, scissors, and the like. Often, a general cutting tool, such as a pair of scissors, is adapted for a particular purpose without departing from its essential design. For example, a child may use a pair of plastic scissors to cut construction paper or a chef may use a pair of kitchen shears to cut herbs or break down poultry. In both instances, the basic concept of pivotally joined blades whose cutting edges are opposed, yet complementary, is used as the foundational concept from which each tool is individually fashioned. Although a variety of context-specific tools—whether scissors, knives, or other cutting tools—can be generated according to the foregoing concept, the resultant cutting devices are generally linked by the common thread of requiring the user to see what she is cutting to accurately, knowingly, and/or specifically cut a target object.

However, direct access—whether visual or physical—to some target objects may be limited. Absent removing physical obstructions to allow for direct line of sight, there are few options available to enable a user to accurately, knowingly, and/or specifically cut an object obstructed from view. Particularly, handheld devices for locating and specifically cutting a target object are lacking.

Accordingly, there are a number of disadvantages with cutting instruments that can be addressed.

BRIEF SUMMARY

Embodiments of the present disclosure solve one or more of the foregoing or other problems in the art of handheld apparatuses for probing and cutting specific targets. An exemplary handheld apparatus for probing and cutting can include an elongate member with a first end associated with a probe and a blade. The probe can include a target interaction surface and can be selectively movable between a retracted state, a probing state, and a target acquisition state. The blade can include a cutting edge and can be selectively movable between a retracted position and an extended position.

Apparatuses for probing and cutting as disclosed herein can also include a handle associated with the second end of the elongate member. The handle can include a first manually operated control operably connected to the probe and configured to move the probe between the probing state and the target acquisition state when the first manually operated control is engaged and/or disengaged. The handle can also include a second manually operated control operably connected to the blade. The second manually operated control can be configured to move the blade between the extended position and the retracted position when the second manually operated control is engaged and/or disengaged.

Apparatuses for probing and cutting, as disclosed herein, can be used in various ways and may have particular applications, for example, as surgical tools within a surgical system for performing carpal tunnel release surgery. Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which:

FIG. 3A illustrates a side view of the apparatus of FIG. 2D having a blade in an extended position according to one or more embodiments of the present disclosure.

FIG. 3B illustrates a front view of the apparatus of FIG. 2D.

FIG. 3C illustrates a side view of the apparatus of FIG. 2B having a blade in a retracted position according to one or more embodiments of the present disclosure.

FIG. 3D illustrates a front view of the apparatus of FIG. 2B.

FIG. 4A illustrates a side view of an apparatus having a rotating probe and blade according to one or more embodiments of the present disclosure.

FIG. 4B illustrates a front view of the apparatus of FIG. 4A.

FIG. 4C illustrates a side view of an apparatus having a blade recessed between tines of a probe, the blade being movable to an extended position according to one or more embodiments of the present disclosure.

FIG. 4D illustrates a front view of the apparatus of FIG. 4C.

FIG. 7A illustrates an apparatus of the present disclosure probing a target site according to one or more embodiments of the present disclosure.

FIG. 7B illustrates the apparatus of FIG. 7A identifying the target site according to one or more embodiments of the present disclosure.

FIG. 7C illustrates the apparatus of FIG. 7A acquiring the target site according to one or more embodiments of the present disclosure.

FIG. 7D illustrates the apparatus of FIG. 7A acquiring the target site with a blade in an extended position according to one or more embodiments of the present disclosure.

FIG. 7E illustrates the apparatus of FIG. 7A cutting the target site according to one or more embodiments of the present disclosure.

DETAILED DESCRIPTION

Figure 1:
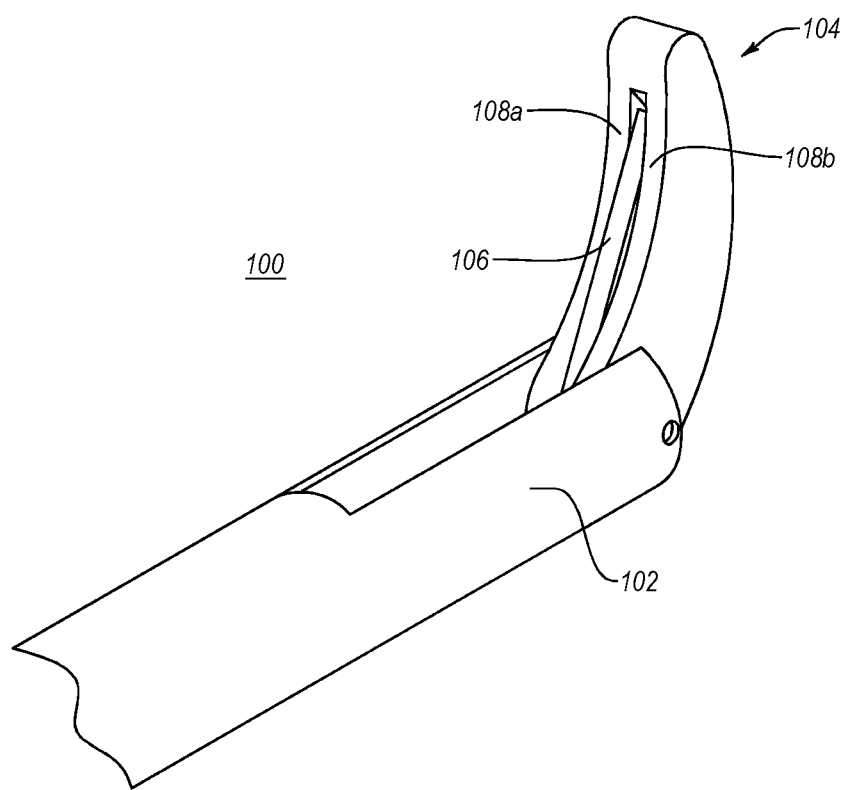
FIG. 1 illustrates a perspective view of an apparatus for probing and cutting according to one or more embodiments of the present disclosure.

Overview of Surgical Cutting Tools and Methods of Use

In general, surgical procedures are performed to treat pathological diseases (e.g., appendectomy, lobectomy of a cancerous lung, etc.), help improve bodily function or appearance (e.g., plastic or reconstructive surgery), or otherwise repair the body (e.g., repair a ruptured organ or serious injury). A plethora of surgical procedures have been created and modified over the years and employ a wide variety of surgical tools and surgical methods. Historically, most surgical procedures fell into the category of "open surgery," which involves the surgeon making a long incision in the patient's body through which surgical instruments are introduced and also through which the surgeon visualizes the surgery. This type of surgery is particularly invasive and generally requires long healing time and extended hospital stays, but it is also associated with an increased risk of infection, likely due to the surgical site—which is normally closed off from the environment—being open and exposed to the elements and any associated infectious agents.

Recently, advances in imaging technologies, electronics, and robotics have provided surgeons with minimally invasive surgical options to replace or complement open surgery. For example, endoscopes—a type of medical device having a light and a camera—are widely used in minimally invasive surgical procedures to provide the surgeon with a view of the surgical site via the endoscopic camera. The endoscope is introduced to the surgical site through a small incision, and the endoscopic light illuminates the surgical site while the endoscopic camera transmits a real-time (or near real-time) display of the surgical site to a monitor in the surgical theatre. Sometimes a second small incision is made near the surgical site through which surgical instruments are introduced, but a single incision may be used to introduce both the endoscope and the surgical instruments. The surgeon may then perform the surgery, viewing the surgical site on the monitor as opposed to through the open surgical site as would be done in an open surgery approach.

In many instances, endoscopic surgeries are beneficial over open surgery procedures because they allow for small incisions instead of a larger incision. The small incisions may decrease the healing time, and may reduce the length of hospital stay. There also tends to be a decreased risk for infection for endoscopic surgeries.

Endoscopes are not the only medium by which image-guided surgery may be performed. Additional options include, as non-limiting examples, the use of ultrasound systems, computed tomography scanners, magnetic resonance imaging scanners, and the like. Each of these have their own particular set of drawbacks. Some of the foregoing imaging devices require the patient to be administered a contrast dye, which can, in some circumstances, cause an allergic reaction, and which are typically expensive. Additionally, magnetic resonance imaging scanners and computed tomography scanners are expensive and require specially-trained technicians to operate the device. In general, each of the aforementioned image-guided surgical devices add an additional layer of expense to the patient, and in some cases, the use of these devices is redundant or altogether unnecessary.

As a particular example comparing and contrasting open surgery and minimally invasive surgical tools and techniques, carpal tunnel release surgery involves the incision of the transverse carpal ligament (TCL) and may be performed using either an open surgery approach or endoscopically. In an open surgery approach, the physician—typically a surgeon—makes an incision in the skin, subcutaneous tissue, and palmar fascia of the patient's palm to directly access and cut the TCL. This procedure is relatively invasive and requires cutting multiple tissues to complete the surgery, and because the incised tissue is located on the patient's palm, the surgery can result in a drawn out and painful recovery.

Alternatively, carpal tunnel release surgery may be performed as a minimally invasive surgery using an endoscope. The endoscope is introduced at the patient's wrist and moved to the surgical site at which time a specialized cutting tool is either introduced at the same site as the endoscope or at a second point located on the palm. In either case, the endoscope is used to visualize the TCL, and the cutting tool is used to cut the TCL from underneath. This type of surgery typically results in faster patient recovery when compared to the open surgical approach.

Handheld Apparatuses for Probing and Cutting and Methods of Use

In one or more embodiments of the present disclosure, a handheld apparatus is disclosed that can be adapted for use as a surgical tool, and which can be used in, for example, carpal tunnel release surgery. In such embodiments, the surgical tool comprises a probe pivotally connected to a first end of an elongate member (see, for example, FIG. 1). The probe comprises a TCL interaction surface that is obscured when the probe is in the retracted state and, in at least some embodiments, is at least partially obscured when the probe is in a probing state. The TCL interaction surface is exposed to the TCL (at the very least) when the probe is in the target acquisition state. The blade includes a cutting edge that is at least partially associated with the elongate member when the blade is in the retracted position (see, for example, FIG. 2A). The blade is at least partially associated with the probe when the blade is in the extended position (see, for example, FIG. 2D). The cutting edge of the blade is exposed to the TCL when the blade is in the extended position. In some embodiments, the probe may also be in the target acquisition state when the cutting edge of the blade is exposed to the TCL. The surgical tool further provides a handle associated with the second end of the elongate member that includes a first manually operated control operably connected to the probe and a second manually operated control operably connected to the blade.

Such exemplary surgical tools may be used to transect anatomic structures and may particularly be used to perform carpal tunnel release surgery with or without the assistance of image-guided surgical tools. In one or more implementations, a surgical tool as described herein is introduced to a surgical site (e.g., the wrist) and the probe is advanced and activated (i.e., advanced from a retracted state to a probing state). The activated probe pivots away from the elongate member, pressing against the ribbed or underside surface of the TCL. Upon extending the probe past the TCL, the probe pivots to a target acquisition state, whereby the probe is withdrawn until the distal margin of the TCL is acquired by the probe. The blade may then be moved into the extended position such that translocation of the surgical tool toward and/or across the TCL results in the cutting edge of the blade severing the TCL.

In one or more implementations, a surgical tool is provided that is substantially similar to that described above. However, in one or more implementations, the probe does not pivot (see, for example, FIG. 8). Rather, the probe is fixed with respect to the elongate member, and the blade is extendable and/or retractable. Such an exemplary surgical tool as described herein is introduced to a surgical site (e.g., the wrist) and the probe is advanced. As the probe is advanced, the probe presses against the ribbed or underside surface of the TCL. Upon extending the probe past the TCL, the probe is configured to engage the distal margin of the TCL. The blade may then be moved into the extended position such that translocation of the surgical tool toward and/or across the TCL results in the cutting edge of the blade severing the TCL.

Referring now to the figures, FIG. 1 illustrates a perspective view of an apparatus 100 for probing and cutting according to one or more embodiments of the present disclosure. An apparatus 100 includes an elongate member 102, a probe 104 associated with the elongate member 102, and a blade 106 associated with the elongate member 102. As illustrated, the blade 106 is at least partially associated with the probe 104, being partially disposed between two tines 108a, 108b comprising the probe 104.

Figure 2A:
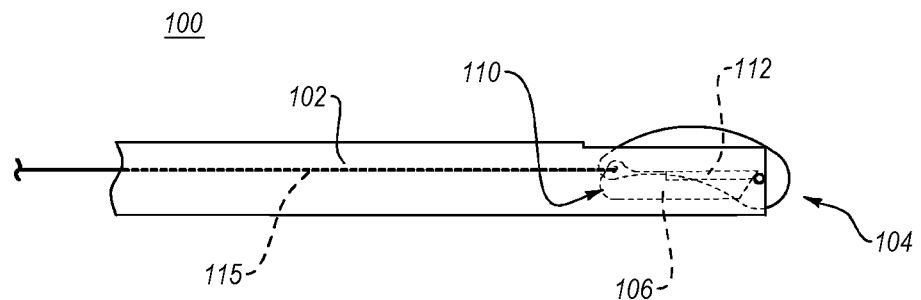
FIG. 2A illustrates an apparatus for probing and cutting in an undeployed state according to one or more embodiments of the present disclosure.

The apparatus 100 of FIG. 1 is depicted with the probe 104 in a probing state and the blade 106 in an extended position. FIGS. 2A-2D illustrates various positions and states of deployment that can be accomplished by apparatus 100 according to one or more embodiments of the present disclosure. For example, FIG. 2A illustrates apparatus 100 in a fully undeployed state. That is, as depicted in FIG. 2A, apparatus 100 includes a probe 104 in a retracted state and a blade 106 that is in a retracted position, a configuration that may for the purposes of this description be generally referred to as an undeployed state.

In a retracted state as depicted in FIG. 2A, the probe 104 is, in one or more embodiments, bent towards the elongate member 102, placing the target interaction surface 110 of probe 104 proximate to the elongate member 102. In this position, the target interaction surface 110 is at least partially obscured from a target. In a retracted position, the blade 106 of FIG. 2A is at least partially associated with elongate member 102. In some embodiments, the cutting edge 112 of blade 106 is buried within the body of elongate member 102 to prevent the cutting edge 112 from unintentionally and/or prematurely interacting with a target or other surrounding structures. In some embodiments, blade 106 is recessed within the elongate member 102 and cutting edge 112 is occluded by the probe 104, the cutting edge 112 being positioned within a recess of probe 104, as shown in FIG. 2A. In other embodiments, the cutting edge 112 of blade 106 is resting on a guard formed on the surface of the elongate member 102 or is otherwise obscured or occluded from a target.

Figure 2B:
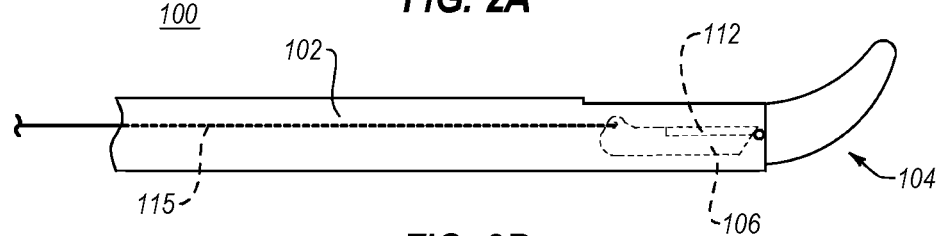
FIG. 2B illustrates the apparatus of FIG. 2A in a partially deployed state according to one or more embodiments of the present disclosure.

Referring now to FIG. 2B, illustrated is apparatus 100 in a partially deployed state according to one or more embodiments of the present disclosure. As illustrated, the probe 104 is in a probing/target acquisition state, and the blade 106 is in a retracted position. Each of the foregoing embodiments, including those depicted in FIGS. 2A and 2B, act to prevent the cutting edge 112 from unintentionally and/or prematurely interacting with a target or other surrounding structures. This may, additionally, provide a measure of safety when handling the apparatus 100, as the cutting edge 112 is at least partially unavailable (if not entirely so) for interacting with—and thereby cutting—a physician, manufacturer or other individual handling the apparatus.

Figure 2C:
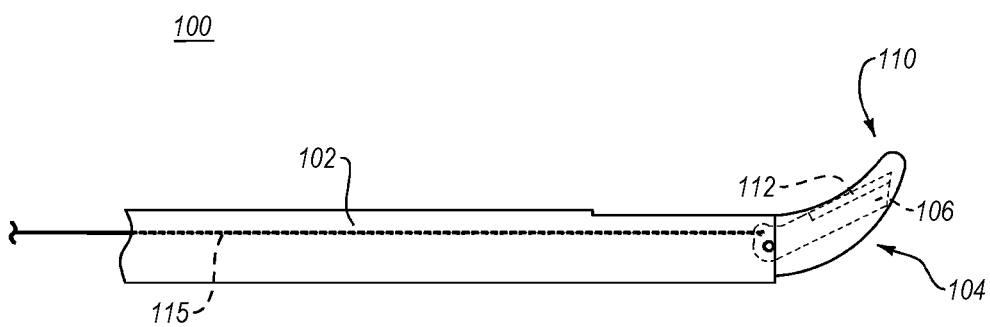
FIG. 2C illustrates the apparatus of FIG. 2A in a partially deployed state according to one or more embodiments of the present disclosure.
Figure 2D:
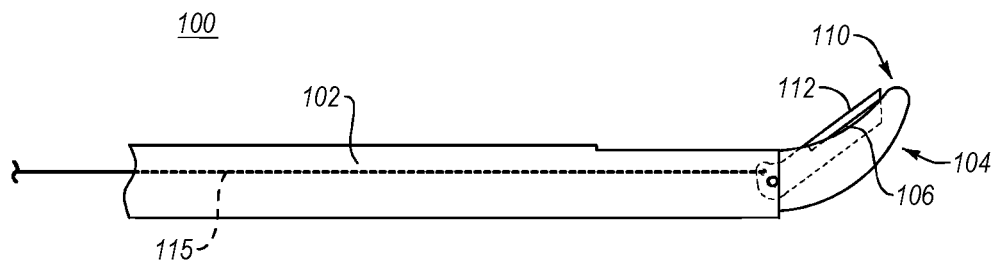
FIG. 2D illustrates the apparatus of FIG. 2A in a fully deployed state according to one or more embodiments of the present disclosure.

Referring now to FIG. 2C, illustrated is apparatus 100 in a partially deployed state according to one or more embodiments of the present disclosure. That is, as depicted in FIG. 2C, apparatus 100 includes a probe 104 in a probing/target acquisition state and a blade 106 in a partially extended position, a configuration that may for the purposes of this description be included as at least one state that falls within the scope of a partially deployed state. As depicted in FIG. 2C, the blade 106 is in a partially extended position, being recessed within probe 104 such that the cutting edge 112 is recessed within the body of probe 104 and unable to interact with and transect elements interacting with probe 104. In one or more embodiments, the blade 106 is moved between a retracted position and an extended position (and any position there between) by mechanical force applied by a push bar 115 and further advanced to a fully extended position as shown in FIG. 2D by, for example, push bar 115 or by any other mechanical means known in the art.

In one or more embodiments, the target acquisition state of probe 104 places the target interaction surface 110 away from elongate member 102. For example, a probe may have an arcuate shape such that it is contoured with a convex side and a concave side, and the target interaction surface of the probe comprises at least a portion of the surface of the concave side of the probe. In a probing state (such as in FIG. 2A), therefore, the target interaction surface faces the elongate member and/or is positioned above the elongate member, and in a target acquisition state, the concave side of the probe—and thereby the target interaction surface—is directed away from the elongate member and/or positioned adjacent to the elongate member as depicted in FIG. 2C. Additionally, or alternatively, the target interaction surface is the surface of the probe that contacts the target in a target acquisition state. Therefore, in one or more embodiments, the target interaction surface may not be defined only with respect to its respective location to the elongate member, but rather, it may be defined with respect to the target in addition to or independent from its relationship to the elongate member.

Additionally, or alternatively, the partially deployed state of an apparatus for probing and cutting may include a probe in a retracted state and a blade in an extended position. This state may also be considered within the scope of a partially deployed state and is exemplary of one or more embodiments where the probe and the blade are independently movable with respect to each other. Though independently movable with respect to each other, the probe and the blade may nonetheless be connected or otherwise associated. For example, the probe and blade may be connected by one or more rods, pins, or similar mechanism known in the art that allows each of the probe and the blade to independently move with respect to the other but also provides a connection between the two components. Further, the probe and blade may be associated with each other in a retracted state and retracted position, respectively, or in a target acquisition state and an extended position, respectively, even though they are independently movable with respect to each other. Alternatively, the probe and blade may not be connected or otherwise directly associated when the disclosed apparatus is in a partially deployed state.

In one or more embodiments, the probe is pivotally joined and/or associated with the elongate member, and transitioning between the retracted state to the target acquisition state involves the probe rotating between states. The rotation and/or pivotal association of the probe with the elongate member may be accomplished by any means known in the art, including, for example, providing torsional energy through the use of a spring or other similar object that stores mechanical energy when twisted, as known in the art, or through the use of one or more elastic materials that are attached to a pivot point on the probe such that when the one or more elastic materials are stretched (e.g., by pulling) a rotation of the probe is induced about an axis.

In one or more embodiments, the probe may not rotate between a retracted state and a target acquisition state, but rather may move by any means known in the art, including, for example, by sliding between the two states.

In one or more embodiments, the probe and the blade may be directly and/or indirectly associated such that movement of one results in movement of the other. In such embodiments, the partially deployed state may not be defined with respect to the juxtaposition of the two states and/or positions of the blade and probe as described above. Instead, the partially deployed state may describe a transition state of the blade from a retracted position to an extended position and the probe from a retracted state to a target acquisition state, or it may describe the transition state between an undeployed state and a fully deployed state. Stated another way, a partially deployed state includes any combination of probe states and blade positions that are not the undeployed state described in FIG. 2A (i.e., the probe in the retracted state and the blade in the retracted position) and that are not the fully deployed state described below with respect to FIG. 2D.

For example, in an embodiment where the probe and the blade are directly associated and/or or move dependently with respect to each other, a partially deployed state may comprise the blade transitioning between the retracted position and the fully extended position and the probe being released from a retracted state but not completely transitioned to the target acquisition state. The blade may be motivated from one position to another by push rod 115. In some embodiments, the probe and blade move dependently with respect to each other, and motivation of the blade by push rod 115 may consequently cause the movement of the probe between states (e.g., between a retracted state, a probing state, and/or a target acquisition state).

As provided above, the probing state may, in some embodiments, represent a transition state and/or intermediate state between the retracted state and the target acquisition state. Accordingly, the partially deployed state may comprise an apparatus having a blade in a retracted position and the probe in the probing state. A probe in the probing state may, therefore, vacillate between the retracted state and the target acquisition state without permanently and/or fully entering either the retracted state or the target acquisition state.

Referring now to FIG. 2D, illustrated is apparatus 100 in a fully deployed state. A fully deployed state comprises the probe 104 in the target acquisition state and the blade 106 in an extended position. In one or more embodiments of the present disclosure, the apparatus 100 is in position and/or configured to engage a target when the apparatus is in the fully deployed state. As shown in FIG. 2D, when the blade 106 is in the extended position (e.g., the cutting edge 112 of blade 106 is no longer recessed within the body of probe 104 as in FIG. 2C) and the probe 104 is in the target acquisition state, the cutting edge 112 of blade 106 is proud of the probe 104. That is, the cutting edge 112 protrudes beyond the edge of probe 104 such that the cutting edge 112 may interact with (and transect) a target.

Though depicted as unobstructed in FIG. 2D, the tip of the blade may, in some embodiments, be recessed within the probe so as to not interfere with or unintentionally cut or poke unintentional targets. Additionally, or alternatively, the tip of the blade may be rounded. Nonetheless, the cutting edge of the blade may still access (and transect) a target.

Referring now to FIGS. 3A-3D, depicted are various views of a probe 104 having a slidable blade 106a according to one or more implementations of the present disclosure. FIGS. 3A and 3B illustrate a side view and a front view, respectively, of a probe 104 having a blade 106a in an extended position. FIG. 3A, for example, illustrates blade 106a in an extended position and at least partially associated with probe 104. As is, perhaps, better illustrated in FIG. 3B, blade 106a is disposed between tines 108a, 108b of the probe 104 when in an extended position. Blade 106a is partially received between tines 108a, 108b. Also depicted in FIGS. 3A and 3B, push rod 115 is associated with a base portion of blade 106a. In some embodiments, the push rod is associated with at least a portion of the probe in addition to or separately from an association with the blade. In other embodiments, the push rod is indirectly associated with one or both of the probe and the blade. It will be appreciated that a separate push rod may be associated with the probe to move the probe between the various states discussed herein.

As illustrated by FIGS. 3C and 3D, when blade 106a is in a retracted position, it is at least partially associated with elongate member 102. During transition between the retracted position and the extended position, blade 106a may slide, in one or more embodiments, along a single axis. In other embodiments, the blade may slide about a longitudinal axis in addition to translocating within one or more transverse coordinate planes. For example, the blade may slide along a single axis from a retracted position within the elongate member to an extended position between the tines of the probe while also moving along a horizontal plane and/or a z-plane, which may function, for example, to lock the blade in an extended position. As an additional example, a blade may be recessed within the elongate body and may be pushed and/or slid upwards away from the elongate body and towards the recess, whereupon the curvature of the tines and/or probe pushes the blade along a horizontal axis until it is in an extended state with the tip of the blade directly associated with the tines and/or probe. In one or more embodiments, a mechanical element may provide the force required to move the blade from a retracted position to an extended position; as depicted in FIGS. 3A-3D, the mechanical element may be push rod 115.

As illustrated in FIGS. 3A and 3C, tines 108a, 108b are arcuate, and as better seen by FIGS. 3B and 3D, the tines 108a, 108b coalesce into an apical segment and form a concave region there between. Also seen in FIGS. 3B and 3D, the concave region formed by the arcuate tines 108a, 108b may, in some embodiments, be disposed about a central axis. In one or more embodiments, the concave region formed by the arcuate tines provides a recess 114 for receiving at least a portion of blade 106a. The recess may, in an embodiment, be defined substantially near the central axis and may similarly be configured to receive blade 106a. Thus, in a broader sense, some embodiments provide a probe 104 in the target acquisition state that defines a recess 114 into which blade 106 may be received when in an extended position. Similarly, the recess 114 may receive blade 106 when the blade 106 is in the retracted position and the probe 104 is in the retracted state.

Additionally, or alternatively, a probe may comprise a singular body, whether arcuate or not, that defines a recess for receiving and/or associating with at least a portion of a blade in an extended or retracted position as described above. The probe may, in some embodiments, occlude one or more parts of the blade and/or may direct a target over its surface to the recess with the blade therein so the blade may transect the target.

FIGS. 4A-4B illustrate various views of a probe 104 associated with a blade 106b that is configured to rotatingly transition between a retracted position and an extended position. The probes 104 of FIGS. 3A-3D and 4A-4D are substantially the same. As can be seen by FIGS. 4A and 4B, blade 106b is in an extended position and, in some embodiments, may be substantially identical to blade 106a in FIG. 3. Referring to FIG. 4A, illustrated is an exemplary embodiment where the probe 104 and blade 106b move dependently with respect to each other. That is, as probe 104 and/or blade 106b is compelled to move from a retracted state or a retracted position, respectively, the other element is consequently compelled in a like manner. Similar to what was discussed in other embodiments, push rod 115 may be directly or indirectly associated with either or both of probe 104 and blade 106b.

Illustrated in FIGS. 4C and 4D, blade 106b is initially disposed entirely within recess 114 of probe 104 (as shown in phantom of FIG. 4C) such that a cutting edge of blade 106b is recessed within the probe 104 and/or does not protrude beyond one or more planes tangential to the surface of tines 108a, 108b (e.g., the cutting edge cannot engage and/or transect a target moving along the surface of tines 108a, 108b without the target entering the recess). Upon activation (shown by the arrows A in FIG. 4C), which in some embodiments is provided by push rod 115, blade 106b may become proud of tines 108a, 108b such that it is positioned to engage and transect an acquired target.

FIGS. 3A-3D and 4A-4D illustrate various particular embodiments that describe the positioning of tines—and the probe, generally—and at least two mechanisms of moving the blade between a retracted position to an extended position. These, however, are not meant to limit the scope of disclosed embodiments to just those depicted in FIGS. 3A-3D and 4A-4D. Any other appropriate mechanisms known in the art for transitioning a blade between a retracted position to an extended position may be adapted herein.

Likewise, FIGS. 3A-3D and 4A-4D illustrate probe 104 as having only two tines. It should be appreciated that probe 104 may have any number of tines, including a single body, and may be arcuate or planar, may hook at an apex of one or more tines, or may have any number or other configuration of tines. In one or more embodiments, the tines are entirely separate and do not coalesce into a continuous apical segment. For example, a probe may have two or more tines, which bound an area (e.g., a recess) that is configured to receive the blade, but which do not otherwise connect at a distal tip. In one or more embodiments, the tips of the tines may touch or are otherwise closely associated but are not fused or directly coupled. Additionally, a probe having a single tine may include a recess that associates with the blade. Such a recess may, for example, be a recessed portion of the singular tine, may be a surface of the tine, or may be an area proximate the single tine that from a perspective view provides a recessed view of the blade with respect to the probe.

Figure 5:
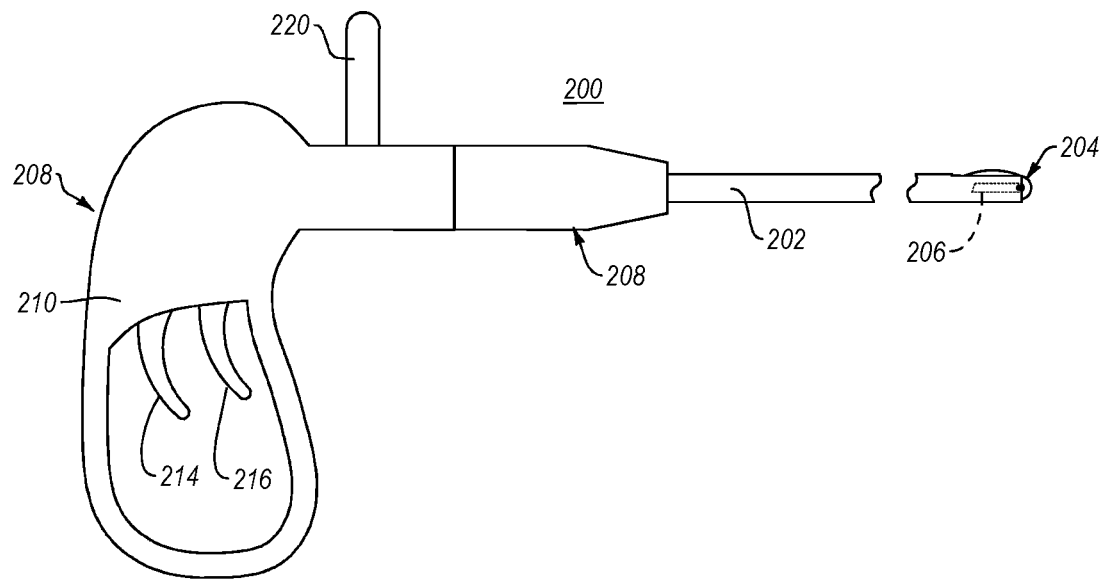
FIG. 5 illustrates an apparatus for probing and cutting comprising a handle according to one or more embodiments of the present disclosure.

Referring now to FIG. 5, illustrated is an apparatus for probing and cutting comprising an elongate member 202 with a first end associated with a probe 204 and blade 206 and a second end associated with handle 208. In some embodiments, handle 208 comprises a gripping region 210—whereby device 200 can be manipulated—a first trigger 214 and a second trigger 216.

In one or more embodiments, the first trigger 214 and the second trigger 216 may be any manually operated control known in the art, including, for example, a dial, switch, slider, button, lever, or combinations thereof. The manually operated control(s) associated with the handle, being in operable connection with the probe and/or blade (e.g., via a push rod such as push rod 115 of FIGS. 2A-2D, 3A-3D, and 4A-4D), operates to control the state and/or position of the probe and/or blade. In one or more embodiments, engagement of the manually operated control(s) causes the probe to move from a retracted state to a probing and/or target acquisition state; additionally, or alternatively, engagement of the manually operated control(s) may cause the blade to move from a retracted position to an extended position or similarly from a recessed position to a protruding and/or cutting position. Additionally, or alternatively, disengagement of the manually operated control(s) causes the probe to move from a target acquisition state to a retracted state (or any intermediate state there between, including a probing state), and/or disengagement of the manually operated control(s) causes the blade to move from an extended position to a retracted position or similarly from a protruding and/or cutting position to a recessed position.

In the embodiments depicted by FIG. 5, the manually operated control is illustrated as two triggers 214, 216 independently and operably connected to probe 204 and blade 206. It should be understood that triggers 214, 216 are exemplary and could comprise any number or type of manually operated control described above and/or known in the art. Further, triggers 214, 216 are understood to have analogous operation in any of the manually operated controls described herein.

In one or more embodiments of the present disclosure, first trigger 214 is operably connected to probe 204. First trigger 214 may, in some embodiments, be in operable connection with probe 204 such that engagement (e.g., depression, extension, or the like) of first trigger 214 selectively moves the probe from a retracted state to the probing state, and to the target acquisition state. In one embodiment, depression of the first trigger causes probe 204 to be released from a retracted state to enter the probing state. Continued and/or increased depression of first trigger 214 may cause probe 204 to proceed to a target acquisition state by any means previously described. As a non-limiting example, probe 204 may be at least partially associated with elongate member 202 in a retracted state, and in response to a minor depression of first trigger 214, probe 204 may partially rotate away from elongate member 202 proportionally to the amount of pressure and/or the degree of depression received and/or experienced by first trigger 214. Continued and/or increased depression of first trigger 214 provides a proportional rotational movement of probe 204 within the probing state towards the target acquisition state. In one or more embodiments, the length of the first trigger movement is directly proportional to the rotational distance between a retracted state and a target acquisition state of the probe. In one or more embodiments, the length of the trigger movement is greater or less than the rotational distance between a retracted state and a target acquisition state of the probe.

As an additional example, the triggers may have one or multiple thresholds such that upon exceeding a first threshold, the associated probe advances a predefined distance or is advanced between states. In some embodiments, the trigger may have two thresholds, a first to move the probe from a retracted state to a probing state and a second to move the probe from a probing state to a target acquisition state. Additionally, or alternatively, a trigger may have two thresholds, a first to move the probe from a retracted state to a probing/target acquisition state and a second to move the blade from a retracted position to an extended/cutting position. In some embodiments, the thresholds may be one or more mechanical thresholds or may, additionally, or alternatively, be a tactile sensation provided through one or more members of the apparatus (e.g., through the one or more triggers, the handle, and/or the gripping region).

In one or more embodiments of the present disclosure, second trigger 216 is operably connected to blade 206 in any analogous way described above with respect to first trigger 214 and probe 204. For example, depression of second trigger 216 causes a proportional advancement of blade 206 from a retracted position to an extended position.

In one or more embodiments, releasing a depressed first trigger 214 and/or second trigger 216 causes the operably connected component to return to an original position (e.g., the retracted state for the probe and the retracted position for the blade). The foregoing may be accomplished in the same proportional manner—but in reverse—as described above when depressing the first and/or second triggers 214, 216, or in some embodiments, releasing the first trigger 214 and/or the second trigger 216 to any degree—or to a threshold degree such as, for example, halfway—causes the operably connected element to immediately and fully return to the original position.

In one or more embodiments, the triggers are binary, and move one or both of the probe and blade from a retracted state/retracted position to a target acquisition state/extended position, respectively. In one embodiment, activation of a binary trigger may release the probe from a retracted state to a probing state, which automatically proceeds to a target acquisition state when the freedom of movement allows for such transition. As a particular example, an activated trigger may move the probe from the retracted state to the probing state, at which time the probe bumps up against the TCL, and upon reaching the distal margin of the TCL (and extending far enough past to allow the probe to fully extend to a target acquisition state), the probe automatically transitions from the probing state to the target acquisition state.

The handle may further comprise a tapered region 208 that comprises a larger diameter region connected to the elongate member 202. In some embodiments, the tapered region 208 may allow a user additional leverage or stability when handling apparatus 200. Tapered region 208 may additionally, or alternatively, provide structural support to elongate member 202 and associated handle 208.

In one or more embodiments of the present disclosure, apparatuses 100, 200 may be sized and shaped for use in minimally invasive surgical procedures. Apparatuses, therefore, may be introduced via any method known in the art, including without limitation via a percutaneous procedure or via a portal opened by incision. An introducer sheath or other surgical device may be employed with apparatuses disclosed herein to assist in and/or complement introduction of the apparatus into the surgical site.

In one or more embodiments of the present disclosure, handle 208 may additionally comprise manually operated control 220 (depicted in FIG. 5 as a lever). In one or more embodiments, an introducer sheath is provided to advance the apparatus from an introduction site to the surgical site. The sheath may include an inner layer directly associated with the apparatus that maintains the probe and/or blade in a retracted state/position and may also provide a pathway to the introduction site and/or the surgical site. Manually operated control 220, when activated causes the inner layer of the introducer sheath to retract away from the probe/blade end of the elongate member, thereby releasing the probe and/or blade and/or allowing for the deployment of the probe and/or blade. Additional manually operated controls (such as triggers 214, 216) may then be operable to control the movement of the probe and/or blade between states/positions as described above. In one or more embodiments, the introducer sheath may comprise a two-phase introducer sheath. In one or more embodiments of the present disclosure, one or more of the sheaths disclosed herein may be translucent and/or transparent.

Figure 6A:
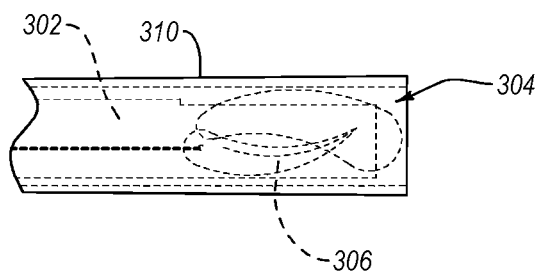
FIG. 6A illustrates a system for introducing an apparatus for probing and cutting to a surgical site, the apparatus being depicted within an introducer sheath according to one or more embodiments of the present disclosure.
Figure 6B:
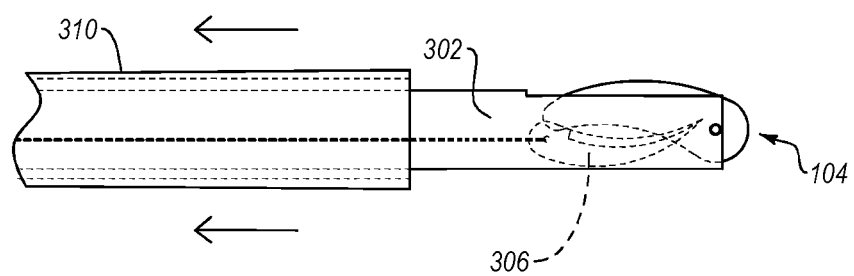
FIG. 6B illustrates the system of FIG. 6A with the apparatus being depicted as extending from the introducer sheath.

FIG. 6A illustrates probe 304 and blade 306 in a retracted state and retracted position, respectively, and directly associated with and covered by sheath member 310. FIG. 6B illustrates movement of sheath member 310 away from probe 304 and blade 306 in the direction shown by the arrows, revealing at least a portion of elongate member 302. The movement of sheath member 310 away from probe 304 and blade 306 may be the result of manually operated control 220 being activated, but in one or more alternative embodiments, sheath member 310 may be a measured length that is shorter than the length required to transit to the surgical site so that as the probe and blade of the apparatus approach the surgical site, the probe/blade end of the apparatus continues towards the surgical site while the sheath member is arrested, thereby divorcing the sheath member and releasing the probe and blade end of the apparatus.

Also depicted in FIGS. 6A and 6B, blade 306 may be crescent shaped and/or arcuate in a similar manner as probe 304. In such embodiments, the blade may be recessed within the probe and may rotate or slide dependently with the probe. Activation of the blade may, in some embodiments, cause the blade to protrude from the protective recess of the probe such that the cutting edge is available to engage and transect a target.

The apparatus referred to herein may comprise a handheld apparatus for probing and cutting. More preferably, the apparatus comprises a medical device for locating and transecting target anatomical structures. In such embodiments, an analogous probe to those described herein is selectively movable between a retracted state and a target acquisition state and an analogous blade is selectively movable between a retracted position and an extended position. The probe may comprise a hook defined by one or more arcuate tines, wherein the concavity of the hook is configured to receive a target anatomical structure when in a target acquisition state. Additionally, or alternatively, a medical device may comprise a handle having first and second manually operated controls—and any other component—as described above.

The medical device and/or apparatuses described herein may also comprise a surgical tool, and in some embodiments, a surgical tool for use when performing carpal tunnel release surgery. FIGS. 7A-7E illustrate an exemplary embodiment of the foregoing. In one or more embodiments, a surgical tool for use when performing carpal tunnel release surgery is introduced into the patient by any of the means described above or as known in the art. This includes, for example, the surgical tool being introduced via a percutaneous procedure that uses an introducer sheath. The surgical tool, though not depicted as such in FIGS. 7A-7E, may be associated with an inner sheath of a two-stage introducer sheath upon introduction at the entry point and for at least part of the transit to the surgical site. In one embodiment, the introduction site is at or near the wrist with the surgical site being located at the base of the patient's palm where the TCL is located.

Referring now to FIG. 7A, illustrated is a surgical tool being advanced along the TCL 420, particularly along an undersurface 422 of TCL 420 that is proximate the dorsal side of the wrist and opposite the palmar side of the wrist. In some embodiments, probe 404 is in the probing state. This may be accomplished through any means disclosed herein, and particularly by depression of a handheld trigger (e.g., a first trigger) operably connected to probe 404. In one or more embodiments, the physician performing the carpal tunnel release surgery depresses the first trigger while advancing the probe along the undersurface 422 of TCL 420. Depression of the trigger translates into the curved (e.g., convex) surface of probe 404 applying pressure to the ligament 420. In one or more embodiments, the surgical tool may be sensitive enough and/or be able to transmit sensory information in such a manner that the physician can feel the probe through the surgical tool bumping and/or traversing the ridges on the undersurface 422 of TCL 420. In one or more embodiments, while the surgical tool is advanced along the undersurface 422 of TCL 420 blade 406 is in a retracted position.

As illustrated in FIG. 7B, the surgical tool is advanced to the distal margin 424 of TCL 420 and encounters the sentinel fat pad just beyond TCL 420. As the resistance against probe 404 decreases, the probe can, in some embodiments, rotate outwards and/or open such that an apical hook formed at the distal end of probe 404, which in some embodiments comprises two curvilinear and/or arcuate metal tines that coalesce into an apical segment, extends just beyond TCL 420. As probe 404 extends beyond TCL 420, probe 404 may additionally rotate and/or open such that it moves into the target acquisition state, and the TCL interaction surface 410 of probe 404 is proximate TCL 420. As illustrated in FIG. 7B, blade 406 is still maintained in a retracted position within the elongate member 402.

Referring now to FIG. 7C, blade 406 is extended into a partially extended position within the probe 404 but does not interact with or transect the acquired TCL. This state, where probe 404 is in the target acquisition state and blade 406 is in the retracted state, is as described above, a partially deployed state of the surgical tool.

As illustrated in FIG. 7D, upon identifying the distal margin 424 with probe 404, blade 406 is advanced from the retracted position to the extended position. In some embodiments, this is accomplished by the physician depressing a second trigger operably connected to blade 406. The second trigger may, when depressed, be a continuous trigger as described above wherein depression of the second trigger enacts a proportional extension of the blade. Additionally, or alternatively, the second trigger may act as a two stage trigger such that upon exceeding a threshold force applied to the trigger, the second trigger advances from a first stage to a second stage, the advancement of which causes the operably connected blade to thrust from a retracted position to an extended position.

In one or more embodiments, activating the second trigger deploys blade 406 into an extended position, the blade 406 being positioned between (and associated with) two tines of the probe 406. With the blade 406 in an extended position and the probe 404 in a target acquisition state, as depicted in FIG. 7D, the surgical tool is considered to be in the fully deployed state. The surgical tool can then be retreated until the cutting edge 412 of blade 406 is proximate and/or interfacing with TCL 420 and the TCL interaction surface of probe 404 is proximate and/or interfacing with TCL 420.

It will be appreciated that the two triggers described above may be any manually operated control, including a multi-stage single trigger. For example, and with respect to the surgical tool depicted in FIGS. 7A-7E, the probe 404 may be moved from a retracted state to a probing state (as shown in FIG. 7A) by depressing a trigger through a first stage. The surgeon may feel a tactile sensation or reach a mechanical resistance point at the end of the first stage. The probe may then be free to probe the TCL 420 in a probing state and to engage the TCL in a target acquisition state (as shown in FIG. 7B). Further engagement of the trigger past the initial tactile response or mechanical resistance point transitions the trigger to a second stage, the result of which is a transition of the blade 406 from a retracted position to at least a partially extended position (as shown in FIG. 7C). In some embodiments, depression of the trigger through the second stage also moves the blade 406 into a fully extended position (as shown in FIG. 7D). In some embodiments, advancing the trigger to a third stage moves the blade from a partially extended position within the probe (as shown in FIG. 7C) to a fully extended position (as shown in FIG. 7D).

Referring now to FIG. 7E, the surgical tool is depicted in the fully deployed state and is drawn towards the TCL 420. As the surgical tool is drawn toward TCL 420, the cutting edge 412 of blade 406 transects TCL 420 into at least two segments 420a, 420b. In at least one embodiment, the TCL interaction surface of the probe acts to secure the TCL as the surgical tool transects the TCL using the cutting edge of the blade. For example, the probe may be hook like and may grab or otherwise secure the TCL before and during transection.

As depicted in FIGS. 7D and 7E, the cutting edge 412 of blade 406 may be positioned relative to the body of elongate member 402 to form an obtuse angle in which the cutting edge 412 of blade 406 may be pressed against and transect TCL 420. The angle formed between the elongate member and the blade may be any obtuse angle, including, for example, any angle between a range of 95° and 165°, any angle between a range of 105° and 150°, any angle between a range of 120° and 150°, any angle between a range of 135° and 150°, any angle between a range of 105° and 135°, or any angle between a range of between a range of 105° and 120°. In one or more embodiments, the cutting edge 412 of blade 406 is substantially orthogonal to TCL 420 as cutting edge 412 transects TCL 420. In one or more embodiments, the surgical tool is drawn across TCL 420 until TCL 420 is completely transected, resulting in distinct and separate segments 420a, 420b.

After TCL 420 is transected—whether entirely or partially—at least one of the probe and the blade, and in some embodiments both of the probe and the blade, are returned to an original position. For example, the probe is moved from a target acquisition state to a probing and/or retracted state and the blade is moved from an extended position to a retracted position. This may be accomplished by any mechanism known in the art. For example, returning the probe and/or blade to the original position may be accomplished by releasing and/or lifting one or more triggers operably connected to the probe and/or the blade. The surgical tool may then be withdrawn from the surgical site via the entry point.

While the foregoing has focused primarily on apparatuses having a body with a pivotally attached probe, it should be appreciated that in some embodiments, the body of the apparatus is structurally contiguous with the probe. Illustratively, the probe may be defined as the distal portion of the body, the probe having a fixed angle with respect to the remainder of the body. In such an embodiment, the probe, itself, is not deployable even though the blade may still be configured to move between retracted and extended positions.

Figure 8:
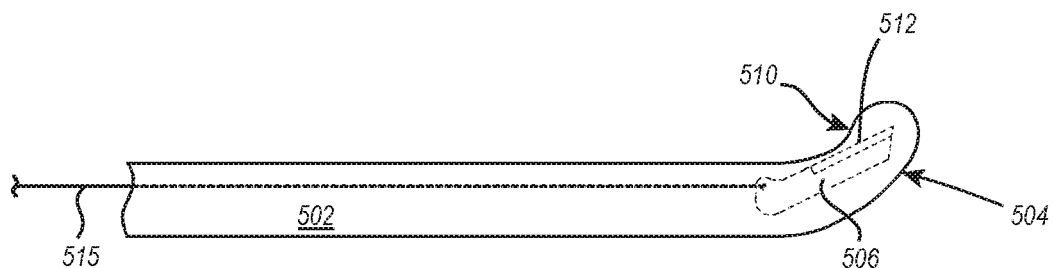
FIG. 8 illustrates a plan view of an apparatus for probing and cutting according to one or more embodiments of the present disclosure.

For example, FIG. 8 illustrates a plan view of an apparatus for probing and cutting according to one or more embodiments of the present disclosure. The apparatus, as illustrated, includes a body having an elongate member 502 and a probe 504 positioned at a distal end of the body and fixedly associated with the elongate member 502. The apparatus additionally includes a blade 506 associated with the elongate member 502. As illustrated, the blade 506 is at least partially associated with the probe 504, being disposed within the probe 504 in a retracted state. Upon activation, the cutting edge 512 of blade 506 can protrude beyond the TCL interaction surface 510 of the fixed angle probe 504.

Figure 9A:
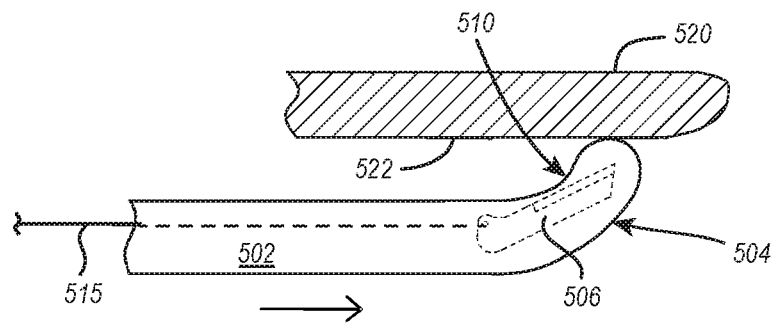
FIG. 9A illustrates an apparatus of the present disclosure probing a target site according to one or more embodiments of the present disclosure.

The apparatus depicted in FIG. 8 can be used in a similar fashion to other apparatuses described herein. For example, the apparatus of FIG. 8 can be used in carpal tunnel release surgery. FIGS. 9A-9E illustrate an exemplary embodiment of the foregoing. Referring now to FIG. 9A, illustrated is a surgical tool being advanced along the TCL 520, particularly along an undersurface 522 of TCL 520 that is proximate the dorsal side of the wrist and opposite the palmar side of the wrist. The probe 504 can be disposed at a fixed angle with respect to the elongate member 502 of the body, such as, for example, any of a 15°, 30°, 45°, 60°, 75°, 90°, 105°, 120°, 135°, 150°, or 165° (as measured from a plane parallel to and transecting the elongate body 502 to the distal tip of the probe 504). In an embodiment, the probe 504 is disposed at a fixed angle between about 15°-90°. In an embodiment, the probe 504 is disposed at a fixed angle between about 30°-60°. In an embodiment, the probe 504 is disposed at a fixed angle between about 30°-45°. In an embodiment, the probe 504 is disposed at a fixed angle between about 45°-60°. The probe 504 being disposed at a fixed angle between about 30°-60°, preferably between about 45°-60°, beneficially allows the probe to engage and efficiently cut target sites.

Figure 9B:
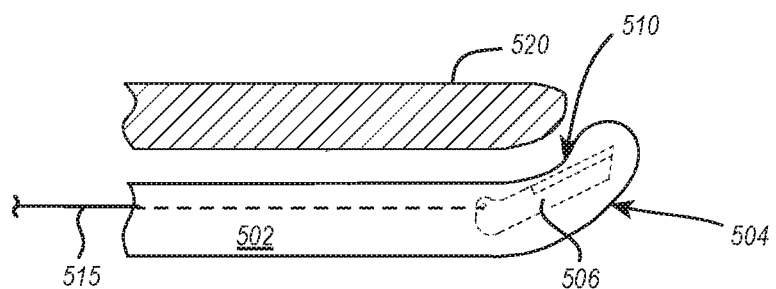
FIG. 9B illustrates the apparatus of FIG. 9A identifying the target site according to one or more embodiments of the present disclosure.
Figure 9C:
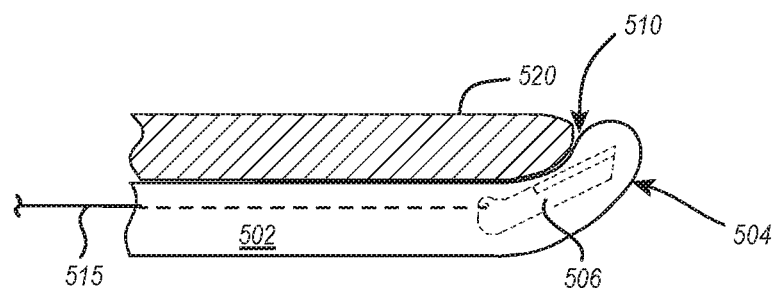
FIG. 9C illustrates the apparatus of FIG. 9A acquiring the target site according to one or more embodiments of the present disclosure.

With continued reference to FIG. 9A, the TCL interaction surface 510 of the probe 504 interacts with the undersurface 522 of TCL 520 as the device is advanced along the TCL 5320 and/or probes the TCL 520. In one or more embodiments, the surgical tool may be sensitive enough and/or be able to transmit sensory information in such a manner that the physician can feel the probe through the surgical tool bumping and/or traversing the ridges on the undersurface 522 of TCL 520. As depicted in FIGS. 9A-9C, blade 506 is in a retracted position while the surgical tool is advanced along the undersurface 522 of TCL 520 so that the blade 506 does not engage and/or transect tissue (including the TCL) while probing.

As shown in FIG. 9B, the surgical tool is advanced to the distal margin of TCL 520 and encounters the sentinel fat pad just beyond TCL 520. As the resistance against probe 504 decreases, the probe can, in some embodiments, extend just beyond TCL 520. As probe 504 extends beyond TCL 520, the TCL interaction surface 510 is proximate TCL 520. As illustrated in FIG. 9B, blade 506 is still maintained in a retracted position within the probe 504.

Figure 9D:
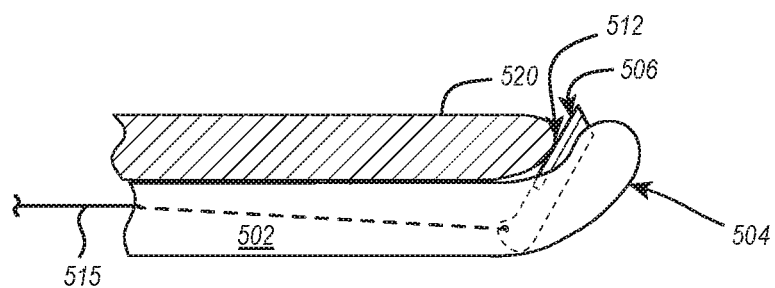
FIG. 9D illustrates the apparatus of FIG. 9A acquiring the target site with a blade in an extended position according to one or more embodiments of the present disclosure.

Referring now to FIG. 9C, the probe 504 is brought into direct interaction with and/or acquires the target TCL 520 such that the TCL interaction surface 510 engages the TCL 520. As illustrated in FIG. 9D, upon identifying the distal margin 524 with probe 504, blade 506 is advanced from the retracted position to the extended position. This can be accomplished by any means disclosed above, including, for example, mechanical or electromechanical operation of the blade. As a non-limiting example, the blade 506 may be placed in an extended position by the physician depressing a trigger operably connected to blade 506 by push bar 515 (as described above with respect to FIGS. 7A-7E).

With the blade 506 in an extended position and the probe 504 in a target acquisition state, as depicted in FIG. 9D, the surgical tool is in the fully deployed state. The surgical tool is now positioned to transect the target TCL 520 upon retraction of the surgical tool.

Figure 9E:
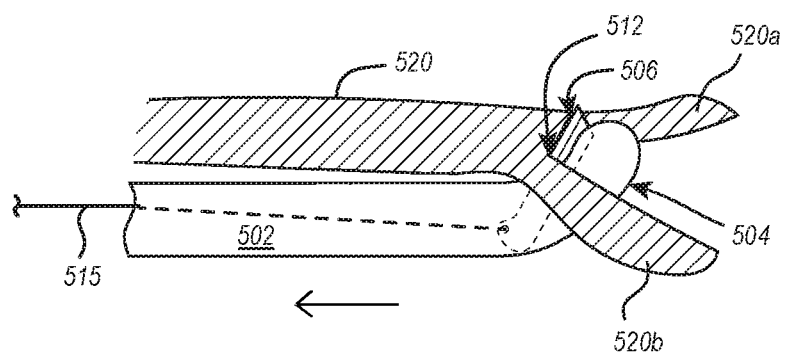
FIG. 9E illustrates the apparatus of FIG. 9A cutting the target site according to one or more embodiments of the present disclosure.

Referring now to FIG. 9E, the surgical tool is depicted in the fully deployed state and is drawn towards the TCL 520. As the surgical tool is drawn toward TCL 520, the cutting edge 512 of blade 506 transects TCL 520 into at least two segments 520a, 520b. In at least one embodiment, the TCL interaction surface of the probe acts to secure the TCL as the surgical tool transects the TCL using the cutting edge of the blade. For example, the probe may be hook like and may grab or otherwise secure the TCL before and during transection.

As depicted in FIGS. 9D and 9E, the cutting edge 512 of blade 506 may be positioned relative to the body of elongate member 502 to form an obtuse angle in which the cutting edge 512 of blade 506 may be pressed against and transect TCL 520. The angle formed between the elongate member and the blade may be any obtuse angle, including, for example, any angle between a range of 95° and 165°, any angle between a range of 105° and 150°, any angle between a range of 120° and 150°, any angle between a range of 135° and 150°, any angle between a range of 105° and 135°, or any angle between a range of between a range of 105° and 120°. In one or more embodiments, the cutting edge 512 of blade 506 is substantially orthogonal to TCL 520 as cutting edge 512 transects TCL 520. In one or more embodiments, the surgical tool is drawn across TCL 520 until TCL 520 is completely transected, resulting in distinct and separate segments 520a, 520b.

After TCL 520 is transected—whether entirely or partially—the blade is returned to an original position. For example, the blade is moved from an extended position to a retracted position. This may be accomplished by any mechanism known in the art. For example, returning the blade to the original position may be accomplished by releasing and/or lifting one or more triggers operably connected to the blade. The surgical tool may then be withdrawn from the surgical site via the entry point.

Attention is now directed to FIGS. 10A-10D, which illustrate cross-sectional views of an apparatus 600 for probing and cutting according to one or more embodiments of the present disclosure. At least some aspects of the apparatus 600 may be similar or identical to the other apparatuses disclosed herein. For instance, the apparatus 600 includes an elongate member 602, a probe 604 associated with the elongate member 602, and a blade 606 associated with the elongate member 602.

Figure 10A:
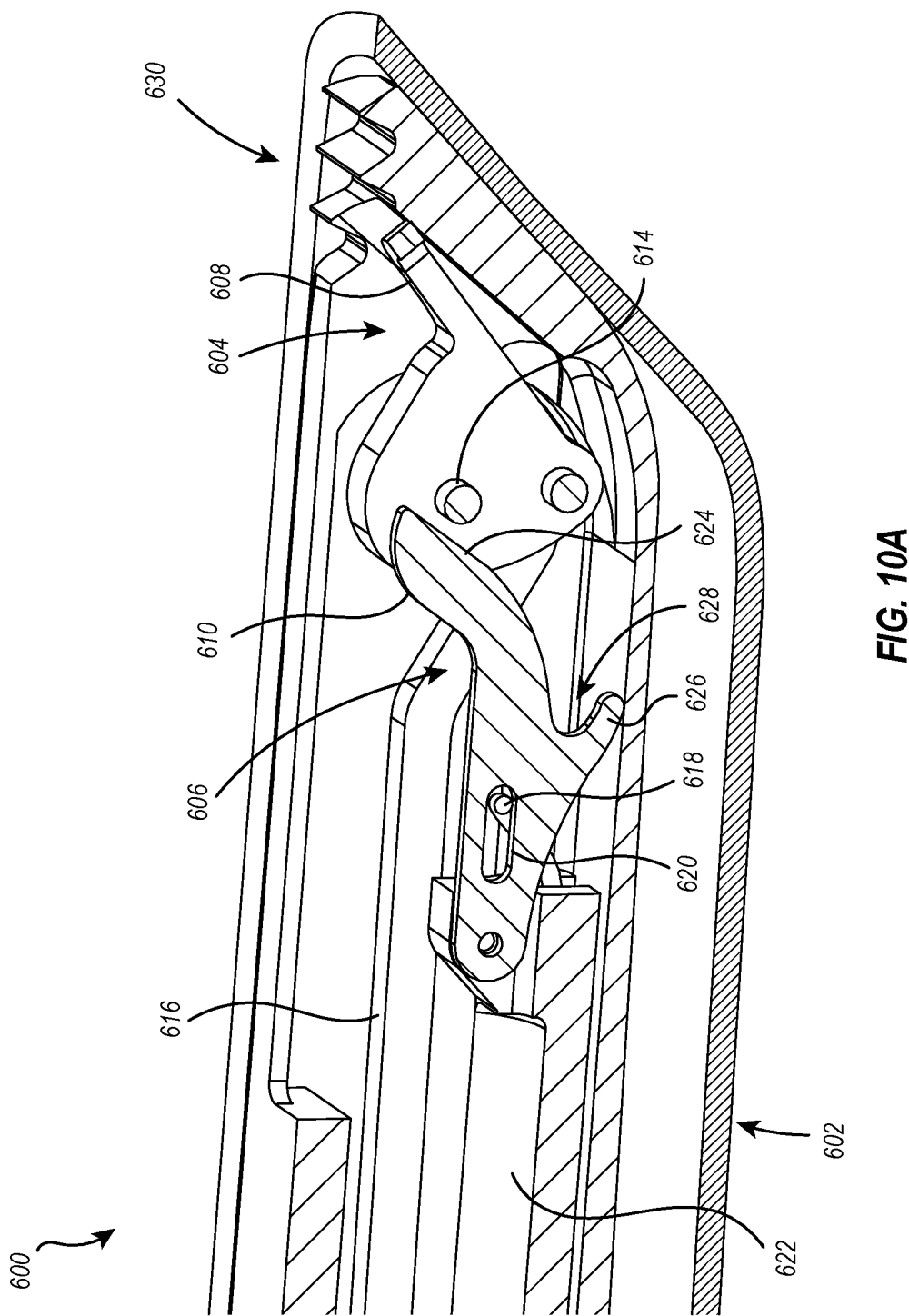
FIG. 10A illustrates an apparatus for probing and cutting in an undeployed state according to one or more embodiments of the present disclosure.

FIGS. 10A-10D illustrate various positions and states of deployment that can be accomplished by the apparatus 600 according to one or more embodiments of the present disclosure. For example, FIG. 10A illustrates the apparatus 600 in a fully undeployed state. That is, as depicted in FIG. 10A, the probe 604 in a retracted state and the blade 606 is in a retracted position.

In a retracted state as depicted in FIG. 10A, the probe 604, in one or more embodiments, is buried within or does not extend out of the elongate member 602. In this position, a target interaction surface 608 of the probe 604 is at least partially obscured from a target. Similarly, in the retracted position, the blade 606 of FIG. 10A is buried within or does not extend out of the elongate member 602 to prevent a cutting edge 610 of the blade 606 from unintentionally and/or prematurely interacting with a target or other surrounding structures.

Figure 10B:
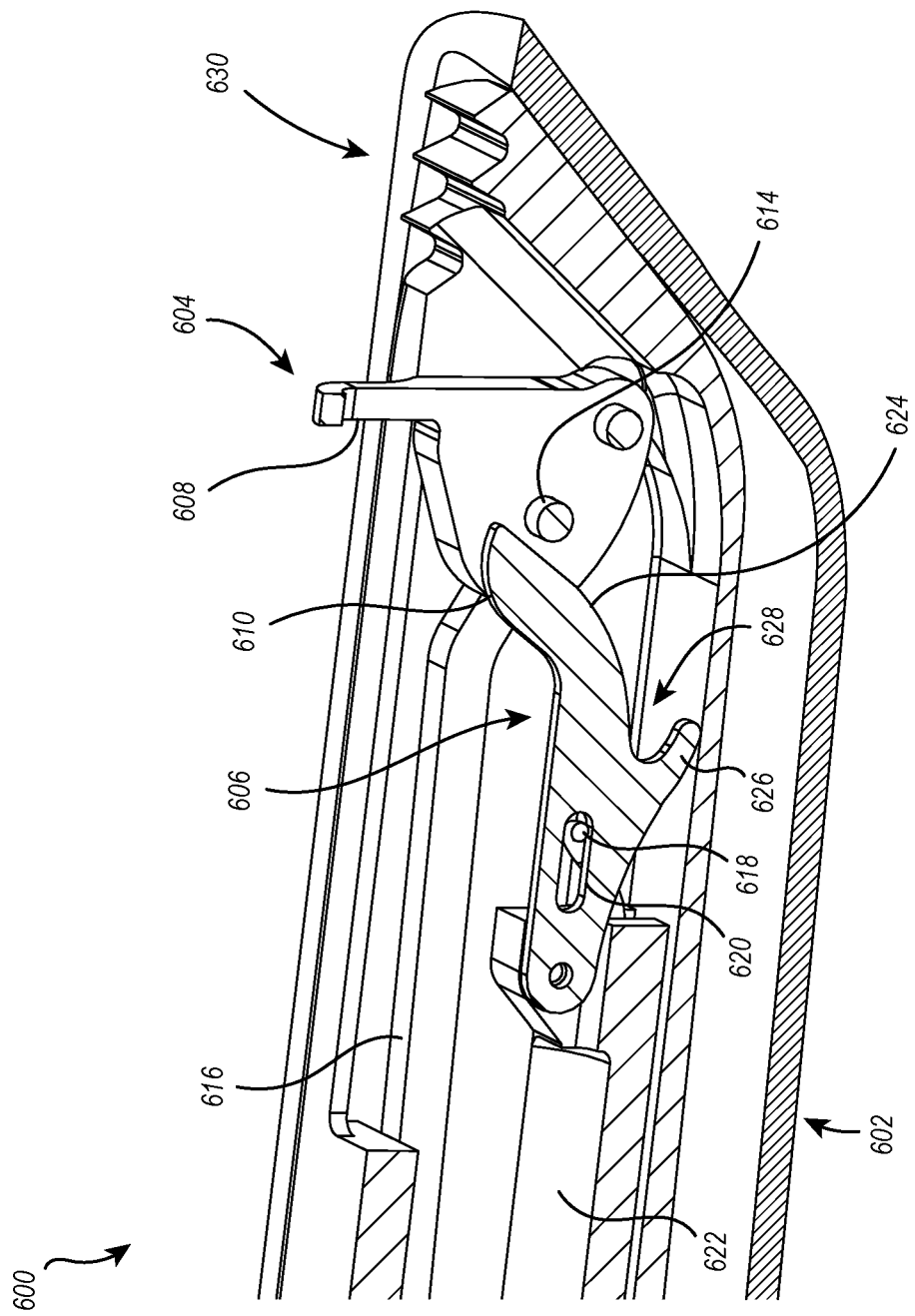
FIG. 10B illustrates the apparatus of FIG. 10A in a partially deployed state according to one or more embodiments of the present disclosure.

Referring now to FIG. 10B, the apparatus 600 is illustrated in a partially deployed state according to one or more embodiments of the present disclosure. As illustrated, the probe 604 is in a probing/target acquisition state. As discussed in connection with the previous embodiments, when the probe 604 is deployed to the probing/target acquisition state, the target interaction surface 608 extends out of the elongate member 602 to enable the target interaction surface 608 to interact with the TCL or other patient tissue. In the partially deployed state shown in FIG. 10B, the blade 606 remains in the retracted position. As a result, the cutting edge 610 is prevented from unintentionally and/or prematurely interacting with a target or other surrounding structures. This may, additionally, provide a measure of safety when handling the apparatus 600, as the cutting edge 610 is at least partially unavailable (if not entirely so) for interacting with—and thereby cutting—a physician, manufacturer or other individual handling the apparatus 600.

To facilitate movement of the probe 604 between the retracted state (FIG. 10A) and the probing/target acquisition state (FIG. 10B), the probe 604 may be movably mounted to the elongate body 602. For instance, a pivot pin 614 may be connected to the elongate body 602 and the probe 604 may be pivotally mounted on the pivot pin 614. An actuator 616, such as a push rod, may be connected to the probe 604. Movement of the actuator 616 may cause the probe 604 to pivot between the retracted state and the probing/target acquisition state. In some embodiments, the actuator 616 may be movable connected to the probe 604 so as to enable relative pivoting or rotational movement therebetween.

Figure 10C:
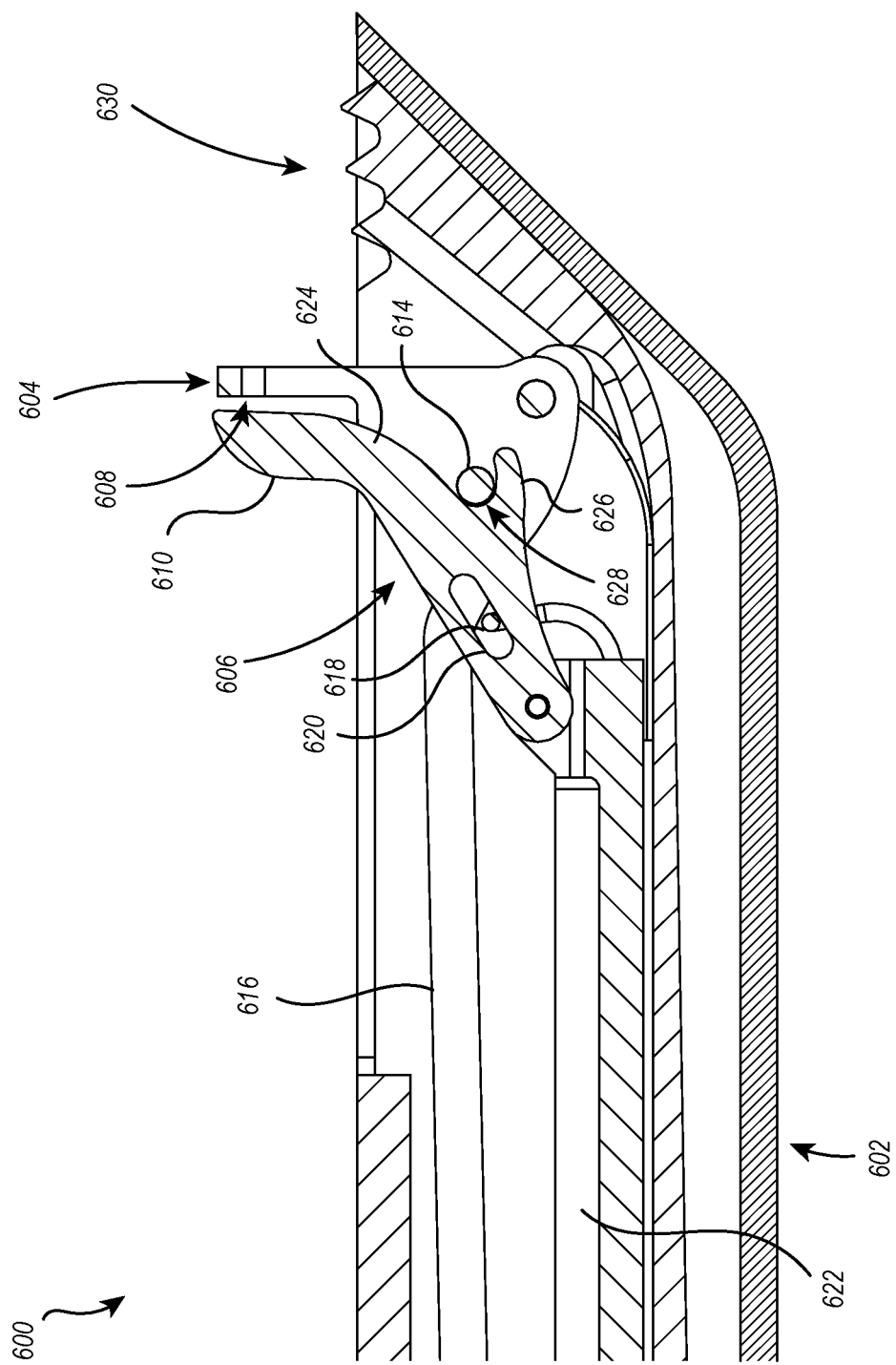
FIG. 10C illustrates the apparatus of FIG. 10A in a fully deployed state according to one or more embodiments of the present disclosure.

Referring now to FIG. 10C, the apparatus 600 is illustrated in a fully deployed state. A fully deployed state comprises the probe 604 in the probing/target acquisition state and the blade 606 in an extended position. In one or more embodiments of the present disclosure, the apparatus 600 is in position and/or configured to engage a target when the apparatus is in the fully deployed state. As shown in FIG. 10C, when the blade 606 is in the extended position, the cutting edge 610 of blade 606 is no longer recessed within the elongate member 602. Additionally, in the illustrated embodiment, the cutting edge 610 is disposed proximal to the probe 604 such that a proximal pulling action on the apparatus will cause the cutting edge 610 to cut tissue in the proximal direction. In other embodiments, the cutting edge may be disposed distally from the probe such that a distal pushing action on the apparatus cause the cutting edge to cut tissue in the distal direction.

To facilitate movement of the blade 606 between the retracted state (FIG. 10A) and the extended position (FIG. 10C), the blade 606 may be movably mounted to the elongate body 602. For instance, the blade 606 may be mounted on a pivot pin 618 via a slot 620 formed therein. As illustrated in FIG. 10C, the slot 620 may extend along a portion of the length of the blade 606. The blade 606 may also be connected to an actuator 622, such as a push rod. Movement of the actuator 622 may cause the blade 606 slide proximally or distally and to pivot. For instance, distal movement of the actuator 622 may cause the blade 606 to slide distally and pivot so as to extend the cutting edge 610 out of the elongate member 602. In contrast, proximal movement of the actuator 622 may cause the blade 606 to slide proximally and pivot so as to retract the cutting edge 610 back into the elongate member 602.

In some embodiments, the actuator 620 may be movable connected to the blade 606 so as to enable relative pivoting or rotational movement therebetween. In some embodiments, as shown in the Figures, an edge 624 of the blade 606 opposite the cutting edge 610 can rest on or otherwise interact with a pivot pin 614 about which the probe 604 pivots. The interaction between the edge 624 and the pivot pin 614 can guide the pivoting movement of the blade 606 as the blade 606 moves between the retracted and extended positions.

In some embodiments, such as that shown in FIG. 10C, the blade 606 may include a spur 626. The spur 626 and the edge 624 of the blade 606 may cooperate to form a recess 628 in the blade 606. As shown in FIG. 10C, the recess 628 may be configured to receive the pivot pin 614 at least partially therein when the blade is moved to the extended position. The interaction between the recess 628 and the pivot pin 614 may limit how far the blade 606 can be extended from the elongate body 602. The interaction between the recess 628 and the pivot pin 614 may also limit or prevent the blade 606 from (further) rotating.

Figure 10D:
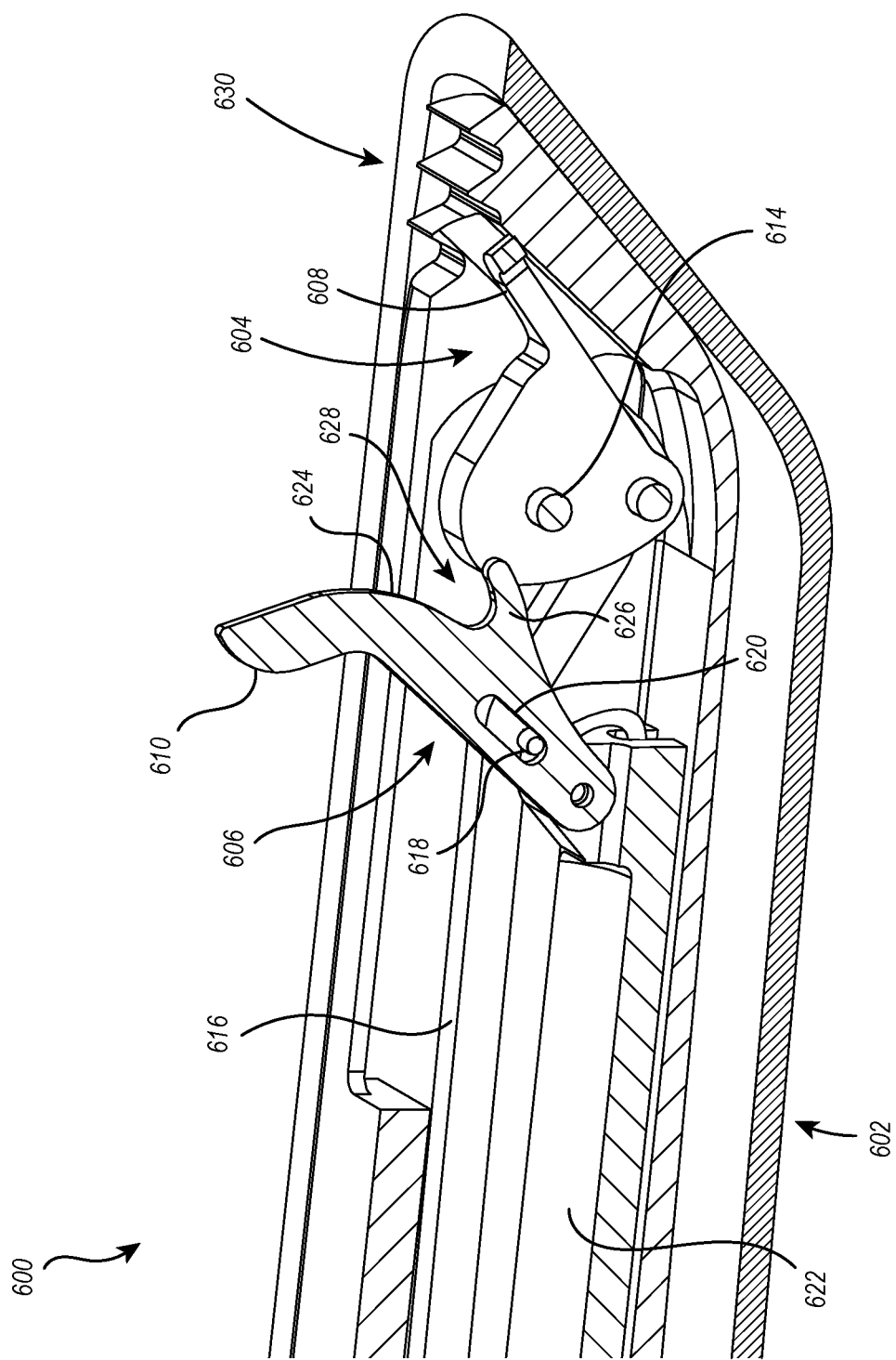
FIG. 10D illustrates the apparatus of FIG. 10A in another partially deployed state according to one or more embodiments of the present disclosure.

Referring now to FIG. 10D, the apparatus 600 is illustrated in another partially deployed state according to one or more embodiments of the present disclosure. That is, as depicted in FIG. 10D, the apparatus 600 includes the probe 604 in retracted/undeployed state (similar to FIG. 10A) and the blade 606 in the extended position (similar to FIG. 10C). From the illustrated embodiment, it will be appreciated that the probe and the blade may be independently movable with respect to each other.

In addition to the probe 604 discussed above, the apparatus 600 may also include one or more additional features to facilitate the location of a target tissue. For instance, as shown in FIGS. 10A-10D, a distal end of the elongate member 602 may include one or more surface features 630, such as ridges, that can be used to interact with tissue to provide tactile feedback to a use of the apparatus 600.

Figure 11:
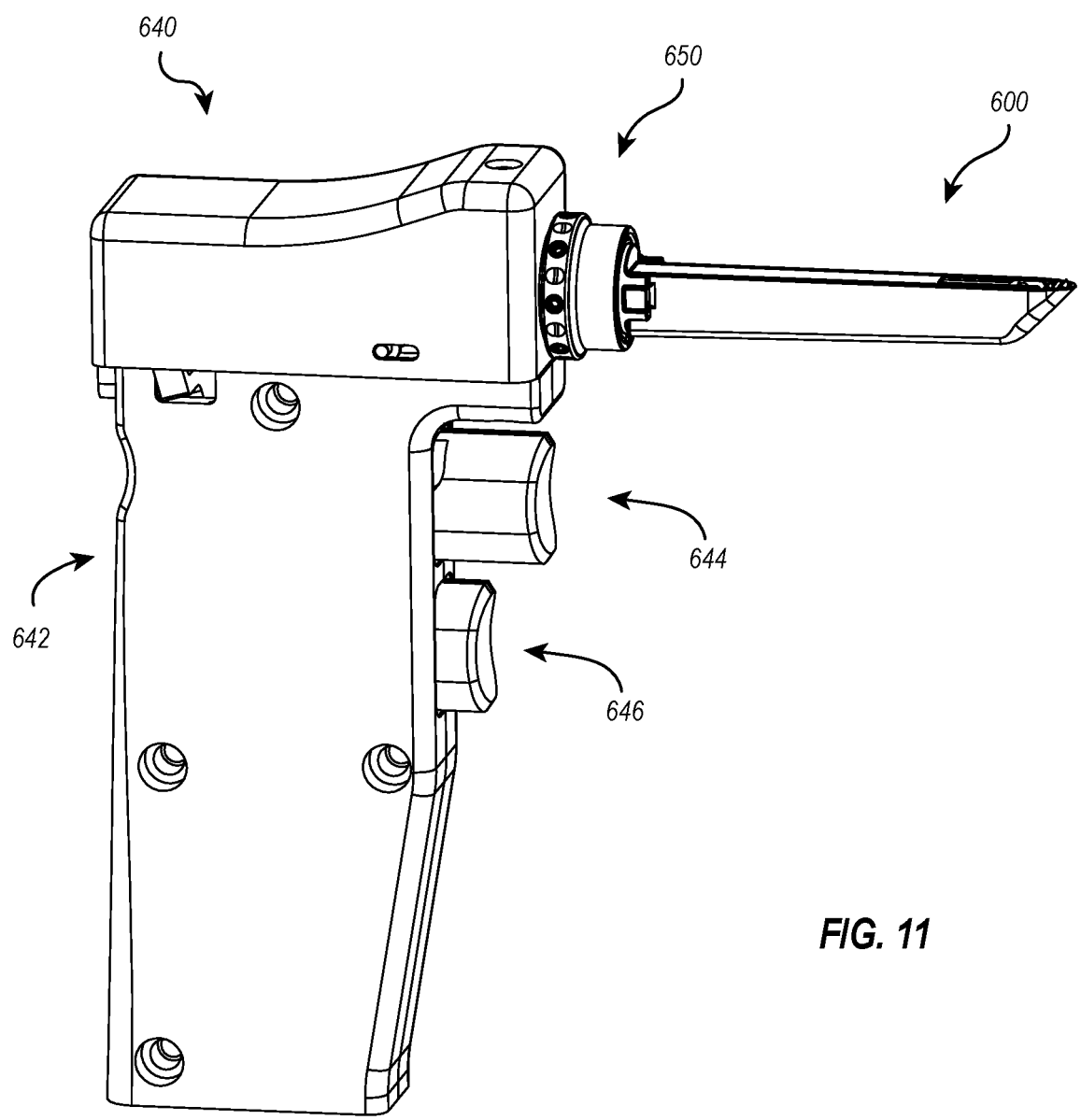
FIG. 11 illustrates an apparatus comprising a handle, an apparatus for probing and cutting, and an adaptor according to one or more embodiments of the present disclosure.

Attention is now directed to FIG. 11, which illustrates the apparatus 600 incorporated into a larger apparatus 640 for probing and cutting. In addition to the apparatus 600, the apparatus 640 also includes a handle 642. In the illustrated embodiment, the handle 642 includes a first trigger 644 and a second trigger 646. The first and second triggers 644, 646 may be used to move the probe 604 and the blade 606 between the undeployed/retracted states to the deployed/extended states discussed above in connection with FIGS. 10A-10D. For instance, each of the triggers 644, 646 may be connected to one of the actuators 616, 622 such that movement of the triggers 644, 646 moves the actuators 616, 622. As discussed above, movement of the actuators 616, 622 results in movement of the probe 604 and the blade 606 between the undeployed/retracted states to the deployed/extended states.

As shown in FIG. 11, the apparatus 640 also includes an adaptor 650. The adaptor 650 is configured to connect the apparatus 600 to the handle 642. As discussed in more detail below, the adaptor 650 may be configured to connect the apparatus 600 to the handle 642 while ensuring or maintaining the apparatus 600 in a desired orientation relative to the handle 642.

Figure 12:
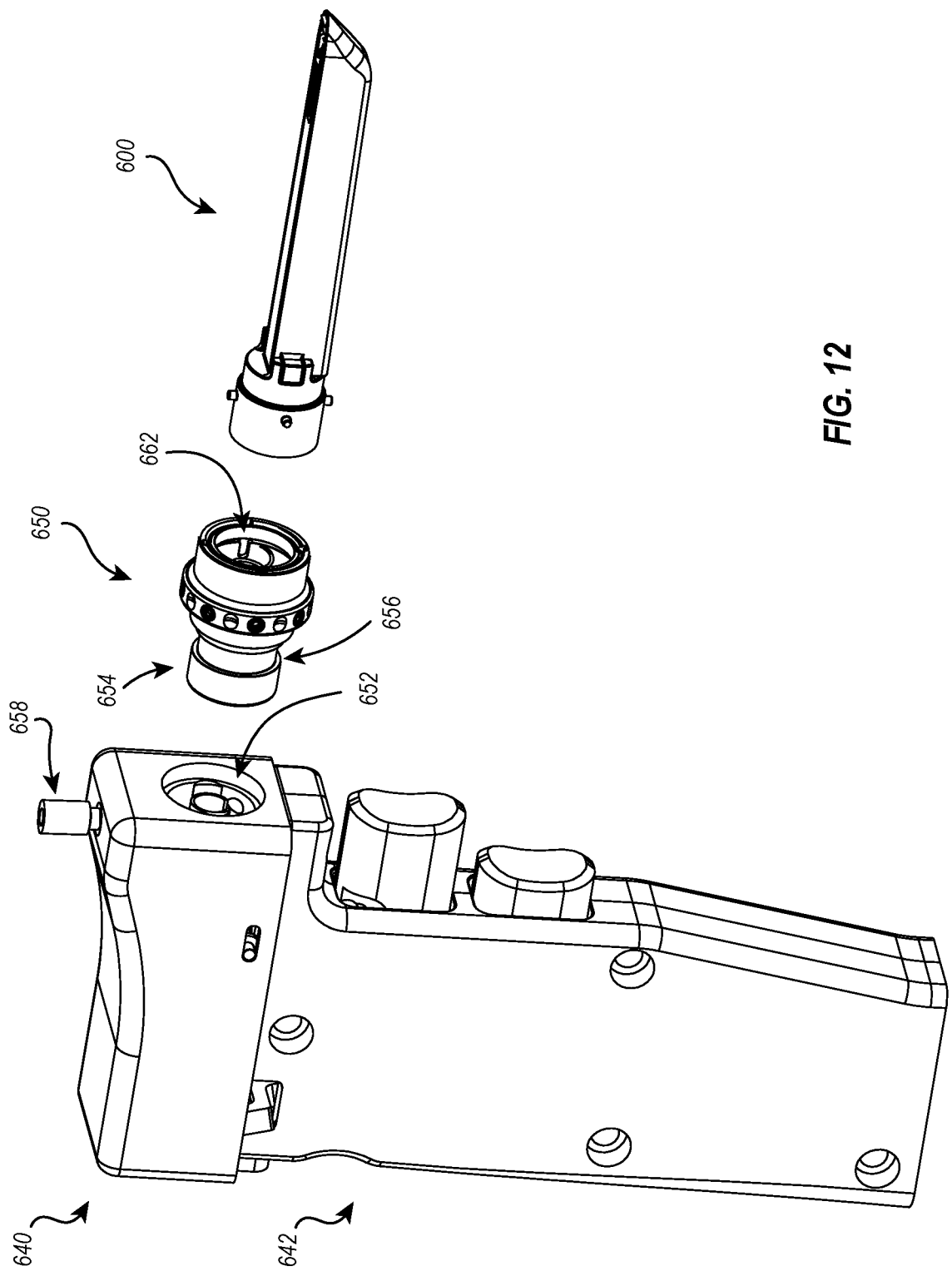
FIG. 12 illustrates a partially exploded view of the apparatus of FIG. 11 according to one or more embodiments of the present disclosure.
Figure 13:
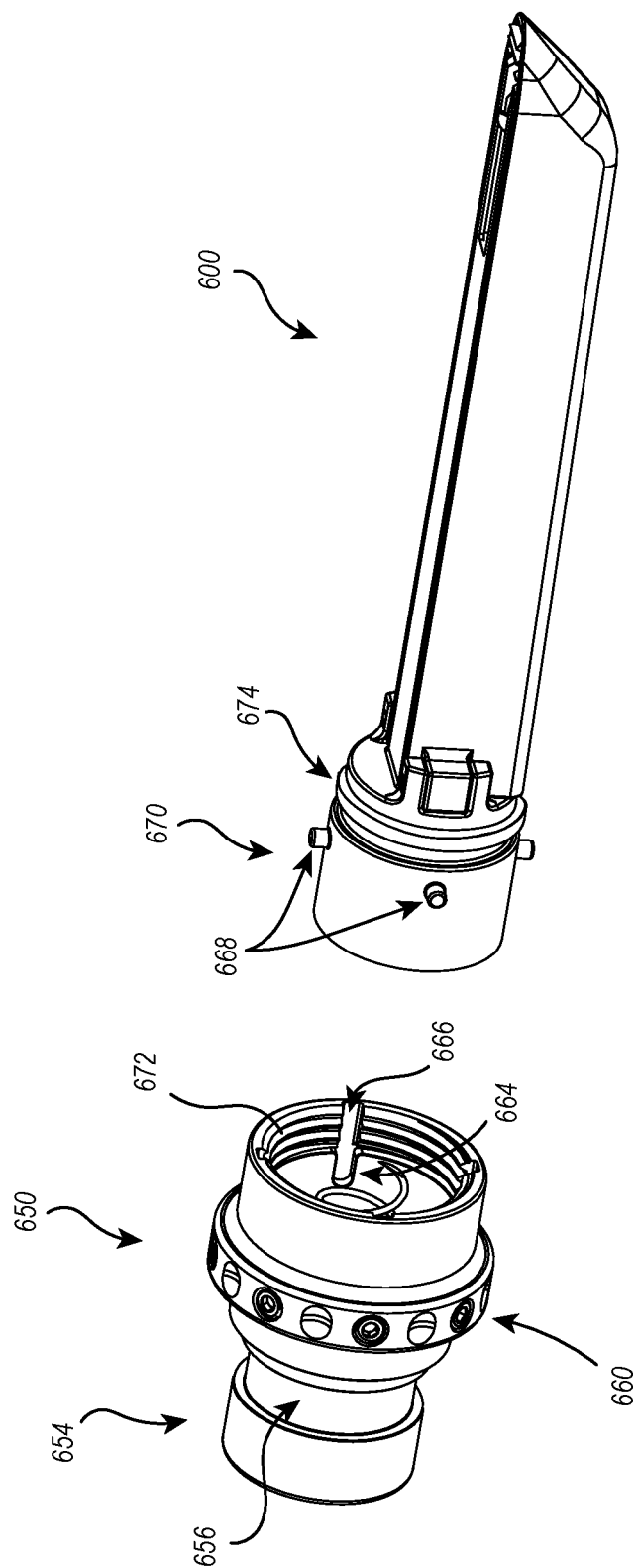
FIG. 13 illustrates a partially exploded view of the apparatus for probing and cutting and the adaptor of the apparatus of FIG. 11 according to one or more embodiments of the present disclosure.

FIGS. 12 and 13 illustrate partially exploded views of the apparatus 640 with and without the handle 642. As can be seen in FIG. 12, the handle 642 includes an opening 652 into a portion of the adaptor 650 can be inserted. More specifically, the adaptor 650 includes a body 654 with an annular groove 656 formed in an exterior surface thereof near a proximal end of the body 654. The proximal end of the body 654 may be inserted into the opening 652 so that the annular groove 656 is disposed within the handle 642. As can be seen in FIGS. 11 and 12, the handle 642 includes a set screw 658 that can be selectively extended into or withdrawn from the annular groove 656 to secure/unsecure the adaptor 650 to/from the handle 642.

In some embodiments, the body 654 of the adaptor 650 and the opening 652 in the handle 652 may have corresponding or mating alignment features to ensure that the adaptor 650 (particularly the body 654 thereof) is secured to the handle 642 in a predetermined or desired orientation. For instance, the opening 652 and the body 654 may have corresponding shapes that only allow the body 654 to be inserted into the opening 652 in a predetermined or desired orientation. In other embodiments, the opening 652 and the body 654 may have a mating key and keyway that only allow the body 654 to be inserted into the opening 652 in a predetermined or desired orientation. In some embodiments, after the adaptor 650 is be connected to the handle 642 in the predetermined or desired orientation, the orientation of the adaptor 650 may be selectively adjusted. For instance, upon loosening of the set screw 658, the adaptor 650 may be rotated (e.g., about an axis thereof) to change the orientation of the adaptor 650 from the predetermined or desired orientation to a second predetermined or desired orientation. Thereafter, the set screw 658 may be tightened to secure the adaptor 650 in the second predetermined or desired orientation.

The adaptor 650 also includes a thumb wheel 660 rotatably mounted on the body 654. Additionally, as shown in FIGS. 12 and 13, a channel 662 extends through the adaptor 650 between proximal and distal ends thereof. When the apparatus 640 is assembled, the actuators 616, 622 may extend through the channel 660.

The body 654 and the thumb wheel 660 include internal surfaces that cooperate to form the channel 662. The internal surfaces of the body 654 and thumb wheel 660 include corresponding slots 664, 666, respectively. While the illustrated embodiment includes multiple slots 664, 666 circumferentially disposed around the channel 662, other embodiments may include a single slot 664 and a single slot 666. In still other embodiments, the number of slots 664, 666 may not be the same as one another. For instance, the body 654 may have a single slot 664 and the thumb wheel 666 may include more than one slot 666. In any event, at least one slot 666 may be selectively aligned with at least one slot 664 (e.g., via relative rotation between the body 654 and the thumb wheel 660.

In the illustrated embodiment, the slots 666 have open proximal and distal ends. In contrast, the slots 664 have open distal ends and closed proximal ends. The slots 664, 666 are configured to receive one or more pins 668 on the apparatus 600. More specifically, the apparatus 600 includes a collar 670 from which the one or more pins 668 extend radially. The collar 670 is sized and configured to be received at least partially into the distal end of the channel 652. Prior to inserting the collar 670 into the channel 652, the slots 664, 666 are aligned with one another (e.g., such that the open proximal ends of the slots 666 are aligned with the open distal ends of the slots 664). The slots 664, 666 can be aligned with one another by rotating the body 654 and/or the thumb wheel 660 relative to one another. Once the slots 664, 666 are aligned with one another, the one or more pins 668 are aligned with the open distal ends of the slots 666 and the collar 670 is inserted into the channel 652.

As the collar 670 is inserted into the channel 652, the one or more pins 668 pass through the slots 666 and into the slots 664. The closed proximal ends of the slots 664 limits how far the collar 670 can be inserted into the channel 670. Inserting the pins 668 into the slots 664, 666 can ensure that the apparatus 600 is connected to the adaptor 650 is a predetermined or desired orientation. For instance, the slots 664, 666 may be disposed around the channel 652 such that the collar 670 may only be inserted into the channel 652 in one orientation. The predetermined or desired orientation may be an orientation about a longitudinal axis of the apparatus 600. As a result, the apparatus 600 may be secured to the adaptor 650 so that the probe 604 and blade 606 are extendable from the elongate member 602 is a particular direction relative to the handle 642.

The apparatus 600 and the adaptor 650 may be selectively secured together via a threaded connection. For instance, the interior surface of the channel 652 may include threads 672 and the exterior surface of the collar 670 may include exterior threads 674. Once the collar 670 is inserted into the channel 652 far enough that the pins 668 are disposed in the slots 664, the thumb wheel 660 may be rotated relative to the collar 670 so as to engage the threads 672, 674. Rotation of the thumb wheel 660 and engagement of the threads 672, 674 may draw the apparatus 600 and the adaptor 650 closer together. Additionally, the rotation of the thumb wheel 660 may misalign the slots 664, 666 such that the pins 668 are secured within the slots 664, which secures the apparatus 600 and the adaptor 650 together.

The apparatus 600 may be disconnection from the adaptor 650 in the reverse process described above. For instance, the thumb wheel 660 may be rotated to disengage the threads 672 from the threads 674. Additionally, the thumb wheel 660 may be rotated to align the slots 666 with the slots 664. When the threads 672, 674 disengages and the slots 664, 666 aligned with one another, the collar 670 may be withdrawn from the adaptor 650. As the collar 670 is withdrawn from the adaptor 650, the one or more pins 668 may pass through the slots 664, 666 and out of the distal open ends of the slots 666.

With the apparatus 600 disconnected from the adaptor 650, the blade 606 and the associated actuator 622 may be removed from the elongate member 602. For instance, the blade 606 and the actuator 622 may be withdrawn from the elongate member 602 through an open proximal end in the elongate member 602. The remainder of the apparatus 600 may be cleaned and sterilized for subsequent uses. The blade 606 and the actuator 622 may be replaced with a new blade and actuator. Thus, part of the apparatus 600 may be reusable (e.g., configured for multiple uses, cleanable/sterilizable) and part of the apparatus may be designed for single use and/or replaceable.

Figure 14:
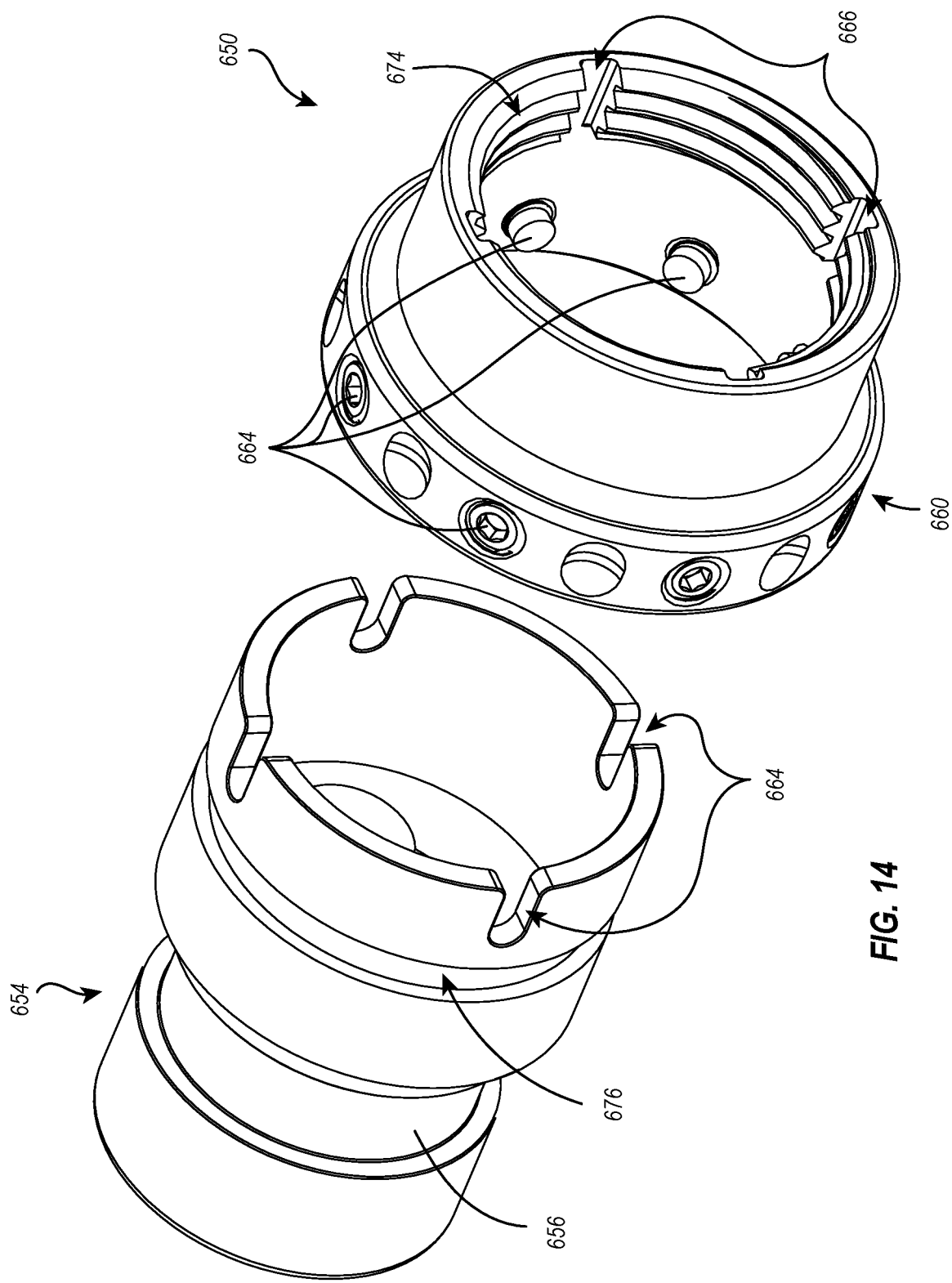
FIG. 14 illustrates a partially exploded view of the adaptor of the apparatus of FIG. 11 according to one or more embodiments of the present disclosure.
Figure 15:
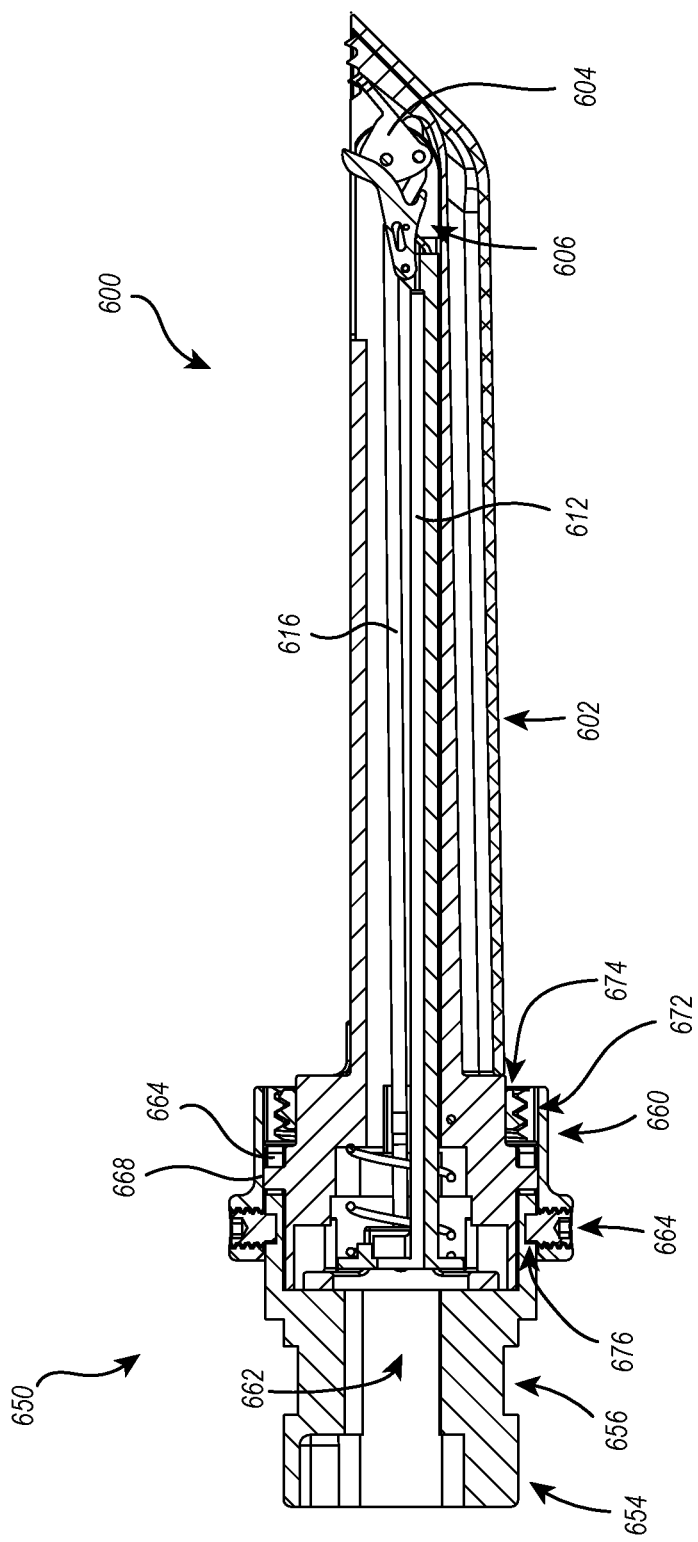
FIG. 15 illustrates a cross-section view of the apparatus for probing and cutting and the adaptor of the apparatus of FIG. 11 according to one or more embodiments of the present disclosure.

Attention is now directed to FIG. 14, which illustrates an exploded view of the adaptor 650. As can be seen, the adaptor 650 includes the body 654 with the annular groove 656 disposed in an outer surface near a proximal end thereof and the slots 664 in the distal end thereof. The body 654 also includes an annular groove 676 in an outer surface thereof between the annular groove 656 and the slots 664. The annular groove 676 is configured to receive therein on or more pins 678 on the thumb wheel 660. As shown in FIG. 14, the one or more pins 678 extend radially inward from the interior surface of the thumb wheel 660. The one or more pins 678 are configured to slide through the annular groove 676 to facilitate relative rotational movement between the body 654 and the thumb wheel 660.

Attention is now directed to FIG. 14, which illustrates a cross-sectional view of the apparatus 600 and the adaptor 650 connected together. As can be seen, the pins 668 are disposed in the slots 664 and the thumb wheel 660 has been rotated so that the slots 666 are not aligned with the slots 664. Rather, the threads 672 on the interior surface of the thumb wheel 660 are disposed adjacent to and block the distal openings of the slots 664. As a result, the pins 668 cannot be removed from the slots 664, which maintains a secure connection between the apparatus 600 and the adaptor 650. On the other hand, the thumb wheel 660 may be selectively rotated to disengage the threads 672 from the threads 674 and aligned the slots 666 with the slots 664 to allow the pins 668 to be removed from the slots 664, thereby disconnecting the apparatus 600 and the adaptor 650 from one another.

Using any of the surgical tools described above in carpal tunnel release surgery provides many benefits over the currently available tools and procedures. For example, the surgical tool can be used in a minimally invasive surgical procedure that only requires a single entry point, whether introduced via an incision or via a percutaneous procedure. This translates into less bleeding, a lower chance of infection, less pain, and less scarring, which typically results in faster patient recovery times when compared to open surgical techniques or even other minimally invasive surgical techniques that require two portals for performing the surgery. Additionally, use of the disclosed surgical tool in carpal tunnel release surgery does not require surgical robotics that are costly and could malfunction during surgery and potentially affect surgical outcome. Further, the disclosed surgical tool does not require—though it may often be used with—an accompanying endo scope or other image-guided surgical instruments (e.g., ultrasound systems, computed tomography scanners, magnetic resonance imaging scanners, etc.). Overall, the disclosed surgical device results in a safer and more simplistic approach to performing carpal tunnel release surgery.

Many of the foregoing advantages are equally relevant to any of the handheld apparatuses disclosed herein. Additional advantages—whether in the particular context of carpal tunnel release surgery or generally relevant—include the ability to advance a probe at or near a target location without damaging surrounding structures. For example, the blade may be in a retracted position during the probing stage whereby the cutting edge is safely occluded, thereby preventing any accidental cutting or snagging of unintended targets.

Also, the probe, in some embodiments, is arcuate such that the probing surface (e.g., the side opposite the target interaction surface) has a convex contour that allows the probe to more naturally and/or smoothly advance through an environment without snagging and/or tearing any surrounding structures. In a target acquisition state of the probe, the convex contour may additionally be configured to purposefully engage a target. Even then, however, some embodiments of the present disclosure provide that when the probe is in the target acquisition state, the blade is in a retracted position, preventing any unintentional cutting from occurring. Upon activation (e.g., extension or protrusion) of the blade, the acquired target may be cut. In this way, the handheld apparatuses of the present disclosure provide a device that enables target specific cutting.

In one or more embodiments of the present disclosure, the probe and/or blade of the handheld apparatus are operably connected to one or more manually operated controls on an associated handle. These manually operated controls activate the probe and may, in some embodiments, independently control the positioning of the blade (e.g., operating the blade between a retracted or extended state). Certain advantages of this include the ability to extend the probe and/or blade at a specific time and/or place followed by retraction of the probe and/or blade so that when the apparatus is withdrawn, no other structures are cut, snagged, or otherwise unintentionally damaged. When used in a surgical setting, this translates into a surgical tool that may be introduced at a distant site and safely advanced to a target site where a target anatomic structure is acquired and severed by a selectively extended surgical blade. The surgical blade and/or probe may then be retracted at the target site followed by being safely withdrawn without further or unintentional interference.

ADDITIONAL EMBODIMENTS

In some embodiments, a handheld apparatus for probing and cutting comprises (i) an elongate member comprising a first end and a second end, (ii) a probe disposed at the first end of the elongate member and comprising a target interaction surface, the probe being fixed at an angle respective to the elongate body, and (iii) a blade associated with the first end of the elongate member and comprising a cutting edge, the blade being selectively movable between a retracted position and an extended position.

In some embodiments of the foregoing handheld apparatus, the cutting edge of the blade is obscured at least partially by the elongate member when the blade is in the retracted position.

In some additional, or alternative, embodiments, the probe further defines a recess configured to receive at least a portion of the blade when the blade is in the extended position.

In some additional, or alternative, embodiments, the handheld apparatus further comprises a handle associated with the second end of the elongate member that is operably connected to the blade by a manually operated control, the manually operated control being configured to extend the blade from a retracted state retracted state when engaged. The manually operated control can, in some embodiments, be selected from the group consisting of: a dial, a switch, a slider, a button, a lever, a trigger, and combinations thereof and can additionally, or alternatively, be configured to cause the blade to pivot towards the retracted state when the first trigger is disengaged.

In some embodiments, a medical device for probing and cutting, comprises (i) an elongate member comprising a first end and a second end, (ii) a probe associated with the first end of the elongate member, (iii) a blade associated with the probe and comprising a cutting edge, the blade being selectively movable between a retracted position and an extended position, and (iv) a handle associated with the second end of the elongate member, the handle operably connected to the blade.

In some embodiments of the foregoing medical device for probing and cutting, the probe comprises a hook defined by one or more arcuate tines and having a recess therein. In some embodiments, the blade is disposed within the recess.

In some embodiments, the probe is associated with the elongate member at a fixed angle. It may be any angle disclosed herein, including, for example, the terminal tip of the probe being disposed at a fixed angle between about 45°-60° relative to the elongate member.

Additionally, or alternatively, the handle can further comprise a manually operated control selected from the group consisting of: a dial, a switch, a slider, a button, a lever, a trigger, and combinations thereof, the manually operated control being operably connected to the blade such that engagement of the manually operated control selectively moves the blade between the retracted position and the extended position.

Any of the foregoing handheld devices, medical tools, and/or surgical tools can be sized and shaped for use in a minimally invasive carpal tunnel surgery.

Abbreviated List of Defined Terms

To assist in understanding the scope and content of the foregoing written description and appended claims, a select few terms are defined directly below.

The term "blade" refers to any sharp instrument known in the art that is configured to cut and can be made of any suitable material, particularly those materials known and used in the art of surgery (e.g., stainless steel, tempered steel, high carbon steel, titanium, ceramic, etc.). A blade, as used herein, includes any appropriately sized and shaped surgical knife, scalpel, lancet, or other sharp surgical instrument suited to the methods described herein. The blades disclosed herein may be re-useable or disposable and may be interchangeable.

For the purposes of this description, the term "introduce" is intended to include any of its common denotative meanings, and particularly in the context of this description, the term "introduce" may refer to inserting an object (e.g., medicine, surgical tool, etc.) into the body of a patient.

The term "introducer sheath" generally refers to a tube that can be introduced into the body and through which medicines, surgical tools, and/or other medically relevant material may be delivered into the body. As used herein, an introducer sheath may be flexible or rigid and may be of any length and gauge as known and used by those having skill in the art, as appropriate. An introducer sheath may additionally comprise a length and gauge sufficient to introduce the disclosed apparatus comprising a deployable probe and blade inside the body, regardless of whether the length and gauge of said introducer sheath is known and used by those having skill in the art. When referenced, an introducer sheath is understood to include cannulas, catheters, and any similar device falling within the scope of this definition. An introducer sheath may include one or more elements as known in the art, including without limitation, a guidewire, a dilator, a sheath, a side tube (with or without a stop cock), a valve, a seal, and/or a locking mechanism. An introducer sheath may be used in a vascular procedure as known in the art wherein the introducer sheath is disposed within the lumen of a blood vessel. Additionally, or alternatively, an introducer sheath may be used in a percutaneous procedure where the introducer sheath is disposed within the body of a patient but outside of the vasculature. Additionally, or alternatively, an introducer sheath may be disposed within the body through an open surgical procedure as known in the art (e.g., cutting any of the epidermis, dermis, subcutaneous tissue, muscle, etc. with a scalpel followed by introduction of the introducer sheath into the body through the incision made by the scalpel).

For the purposes of this description, the term "minimally invasive surgery" as used herein refers to surgical techniques that limit the size of incisions needed and in so doing lessens wound healing time, associated pain, and risk of infection as compared to open surgery techniques as known in the art. This term is meant to include, for example, robotic assisted surgeries and any of the many varieties of endoscopic surgeries known in the art. This term is also meant to include colloquial equivalents such as "band-aid surgery" and "keyhole surgery."

The term "patient" generally refers to any animal under the care of a physician, as that term is defined herein, with particular reference to humans under the care of a surgeon or other relevant medical professional.

The term "physician" as used herein generally refers to a medical doctor, particularly a surgeon. This term may, when contextually appropriate, include any medical professional, including any licensed medical professional, such as a physician's assistant, a nurse, a genetics counselor, a veterinarian, etc.

The terms "position" and "state" as used with reference to a blade and probe, respectively, are made with respect to various stages or conformations. For example, a blade may be in a retracted position or an extended position. A probe may be in a retracted state, a probing state, or a target acquisition state.

Throughout the disclosure, the probe may be referenced in one or more probe states. For example, the probe may be referenced in a retracted state, a probing state, or a target acquisition state. For the purposes of this disclosure, a retracted state includes any initial state of a probe where the probe is drawn substantially toward the elongate member or is otherwise undeployed from an elongate member (see, for example, FIG. 2A). In some embodiments, a probe is nestled within a recess formed within the elongate member when in a retracted state.

For the purposes of this disclosure, a target acquisition state includes any fully extended or fully deployed probe state (see, for example, FIG. 2D). It should be understood, however, that the target acquisition state may also comprise any intermediate state between a retracted state and a fully deployed or fully extended state where the probe attaches, associates, or otherwise acquires a target.

For the purposes of this disclosure, a probing state includes any state between the retracted state and the target acquisition state. In some embodiments, the probing state includes those intermediate states between a retracted state and a target acquisition state where the probe may be used to probe or identify a potential target. A probe in a probing state may be selectively movable between a retracted state and a target acquisition state. In some embodiments, a probing state may be interchangeable with a retracted state. For example, a probe in a retracted state may be used to search for one or more potential targets. In such an embodiment, the probe may not have substantially moved away from the retracted state but may nonetheless be considered to be in a probing state and/or a retracted state. Similarly, a probe may be in a probing state when it is released from a retracted state and is rotated or otherwise moved to identify a target. As the probe rotates or moves away from the retracted state, the probe may identify a target at a given probe position, and without additional rotation or movement from the given probe position, the probe may transition from a probing state to a target acquisition state upon identification of a desired target. Thus, as used herein, a target acquisition state describes those probe states where the probe positively acquires or is otherwise associated with a target, and a probing state can be any probe position between (or outside) the retracted state and the target acquisition state.

Accordingly, in some embodiments, the probe may be in a retracted state when the probe is substantially parallel to an elongate member. If, as provided by some embodiments described herein, the probe is rotated from a retracted state to a target acquisition state, the retracted state can be considered a rotational starting point—or 0° of rotation. In some embodiments, the target acquisition state is any of a 15°, 30°, 45°, 60°, 75°, 90°, 105°, 120°, 135°, 150°, 165°, or 180° rotation (in either a clockwise or counterclockwise direction) from the retracted state, and the probing state includes any intermediate rotation between (and sometimes including) the retracted state and the target acquisition state.

For example, in an embodiment where the target acquisition state is 115° clockwise rotation from the retracted state (e.g., 0°), the probing state may be any angular rotation between 0° and 115°. In some embodiments, the probing state includes all possible points within an available 360° of rotation from the retracted position, and the target acquisition state is defined as the point (e.g., the state) where the probe acquires a target. As adapted from the previous example, the probing state may include all available rotational states of a given probe that can rotate 180° from the retracted state, and upon acquiring a target at, for example, 115° from the retracted state, the probe can be considered to be in a target acquisition state.

In some embodiments, the target acquisition state can be a given state within a range of states. For example, a desired target may be acquired by the probe within a range of states, which may vary between environments, but which nonetheless fall within a defined (or reasonably defined) range of states. As a more particular example, the desired target may be the TCL, which may be acquired by a probe in one or more states between 30° and 180°, or between 45° and 165°, or between 60° and 135°. The probe may, in a probing state, probe for the TCL between any of the foregoing ranges until the TCL is acquired. The state in which the TCL was acquired is the target acquisition state.

In one or more embodiments, the target acquisition state may include the fully extended (or fully rotated) state of the probe away from the retracted state, which in some embodiments may include a target acquisition state that falls within any of the rotational ranges or rotation states described above. In such embodiments, the probing state may be defined as any intermediate state between the retracted state and the target acquisition state.

Throughout the disclosure, the blade may be referenced in one or more blade positions. For example, the blade may be referenced in a retracted position or an extended position. For the purposes of this disclosure, the blade is selectively movable between a retracted position and an extended position.

A retracted position includes any initial position of a blade where the blade is drawn substantially toward or within the elongate member or is otherwise undeployed. In some embodiments, a blade is nestled within a recess formed within the elongate member when in a retracted position.

An extended blade position includes any position of a blade that is not a retracted position. The extended position of a blade, as used herein, includes any partially or fully extended blade position.

Unless defined otherwise, all technical and scientific terms used herein have the same meaning as commonly understood by one of ordinary skill in the art to which the present disclosure pertains. The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

What is claimed is:

1. A device comprising:
    a handle with one or more triggers;
    an apparatus for probing and cutting connectable to the handle, the apparatus comprising an elongated member, a probe, and a blade, the probe and the blade being selectively deployable from the elongate member via activation of the one or more triggers on the handle, the probe being mounted on a pivot pin and configured to pivot on the pivot pin between an undeployed state and a deployed state, the blade being moveable from an undeployed state to an extended state, the blade being configured to interface with the pivot pin to (i) guide the movement of the blade form the undeployed state to the extended state and/or (ii) limit the movement of the blade towards the deployed state; and
    an adaptor configured to selectively connect the apparatus to the handle in a predetermined orientation.

2. The device of claim 1, wherein the adaptor comprises an annular groove in an outer surface thereof and the handle comprises a set screw configured to be selectively inserted into the annular groove to secure the adaptor to the handle.

3. The device of claim 1, wherein the apparatus comprises a collar with one ore more radially extending pin.

4. The device of claim 3, wherein the adaptor comprises one ore more slots in a distal end thereof and configured to receive therein the one or more radially extending pins.

5. The device of claim 4, wherein the collar and the adaptor have mating threads for selectivity securing together the apparatus and the adaptor.

6. The device claim 1, wherein a target acquisition surface of the probe is disposed within the elongate member and extends towards a distal end of the elongate member when the probe is in the undeployed state.

7. The device of claim 6, wherein the target acquisition surface extends out of the elongate member and is pivoted closer to a proximal end of the elongate member when the probe is in the deployed state.

8. The device of claim 1, wherein the blade comprises a spur that at least partially defines a recess in the blade.

9. The device of claim 8, wherein the recess is configured to receive the pivot pin therein when the blade is moved from the undeployed state to the extended state.

10. The device of claim 1, wherein the blade is slidably and pivotally mounted to the elongate member such that the blade moves linearly in a direction generally parallel to a longitudinal axis of the elongate member and pivots about a pivot point as the blade moves between an undeployed state and an extended state.

11. The device of claim 10, wherein the blade comprises a cutting edge, the cutting edge is disposed within the elongate member in the undeployed state and extends out of the elongate member when the probe is in the extended state.

12. The device of claim 1, wherein probe and the blade are configured for independent deployment from the elongate member.

13. The device of claim 1, wherein an orientation of the adaptor is selectively adjustable after connection of the adaptor to the handle in the predetermined orientation.

14. An apparatus for probing and cutting, comprising:
    an elongate member having a proximal end and a distal end;
    a probe rotatably mounted to the elongate member near the distal end thereof, the probe being selectively movable between an undeployed state and a probing state via pivoting about a pivot pin, the probe comprising a target acquisition surface that: (i) is disposed within the elongate member and extends at least partially towards the distal end thereof when the probe is in the undeployed state, and (ii) extends at least partially from the elongate member and is closer to the proximal end of the elongate member when the probe is in the probing state; and
    a blade slidably and pivotally mounted to the elongate member such that the blade moves linearly in a direction generally parallel to a longitudinal axis of the elongate member and pivots about a pivot point as the blade moves between an undeployed state and an extended state, the blade comprising a linear slot extending therethrough and configured to receive a blade pivot pin therein.

15. The apparatus of claim 14, wherein the probe and the blade pivot in generally the same direction when moving between the undeployed states and the probing and extended states.

16. The apparatus of claim 14, wherein the blade is configured to interact with the probe pivot pin to facilitate pivoting of the blade.

17. The apparatus of claim 16, wherein the blade has a recess formed in a surface thereof, the recess being configured to receive the probe pivot pin at least partially therein when the blade is moved to the extended position.

18. The apparatus of claim 17, wherein engagement between the recess in the blade and the probe pivot pin is configured to limit (i) the movement of the blade towards the extended position or (ii) limit rotation of the blade.

19. The apparatus of claim 14, wherein the probe is connected to a first actuator and the blade is connected to a second actuator, wherein substantially linear movement of the first actuator causes the probe to pivot between the undeployed state and the probing state, and substantially linear movement of the second actuator causes the blade to slide and pivot between the undeployed state and the extended state.

* * * * *